United States Patent [19]

Yaegashi et al.

[11] Patent Number: 5,061,800
[45] Date of Patent: Oct. 29, 1991

[54] CAMPTOTHECIN DERIVATIVES

[75] Inventors: Takashi Yaegashi; Satoru Okajima; Seigo Sawada; Kenichiro Nokata; Kenichi Tezuka; Hiroshi Nagata; Teruo Yokokura, all of Tokyo; Tadashi Miyasaka, Kanagawa, all of Japan; Tadashi Miyasaka, Kanagawa, both of Japan

[73] Assignee: Kabushiki Kaisha Yakult Honsha, Tokyo, Japan

[21] Appl. No.: 298,976

[22] Filed: Jan. 19, 1989

[30] Foreign Application Priority Data

Jan. 20, 1988 [JP] Japan .................................. 63-8388

[51] Int. Cl.$^5$ .................... C07D 491/22; A61K 31/47
[52] U.S. Cl. ........................................ 546/48; 546/92; 564/440; 564/441; 564/442; 564/443; 558/413; 558/414
[58] Field of Search ........................... 546/48; 514/283

[56] References Cited

U.S. PATENT DOCUMENTS 4,473,692  9/1984  Miyasaka et al. ...................... 546/48
4,604,463  8/1986  Miyasaka et al. ...................... 544/125

FOREIGN PATENT DOCUMENTS 0085389  4/1986  Japan ...................... 546/48

Primary Examiner—Diana G. Rivers
Attorney, Agent, or Firm—Birch, Stewart, Kolasch & Birch

[57] ABSTRACT

New campotothecin derivatives and a process for preparing same are disclosed, which are represented by the general formula:

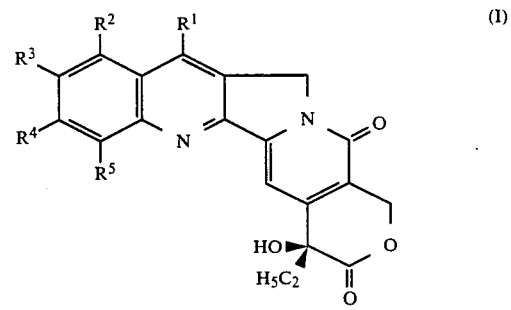

wherein $R^1$ represents a lower alkyl group, $R^2$ represents a hydrogen atom or an amino, hydroxyl, lower acylamino or lower alkoxy group, $R^3$ represents a hydrogen or halogen atom or a lower alkyl, hydroxyl, lower alkoxy, nitro, amino, cyano or di(lower alkyl)amino group, $R^4$ represents a hydrogen or halogen atom or a lower alkyl, hydroxyl, lower alkoxy, lower alkylthio, amino, cyano or di(lower alkyl)amino group, and $R^5$ represents a hydrogen or halogen atom or a hydroxyl or lower alkoxy group, with the proviso that all of the $R^2$, $R^3$, $R^4$ and $R^5$ substituents should not be a hydrogen atom and also that if any one of the $R^2$, $R^3$, $R^4$ and $R^5$ is a hydroxyl or lower alkoxy group, all of the other three substituents should not be a hydrogen atom.

3 Claims, No Drawings

CAMPTOTHECIN DERIVATIVES

BACKGROUND OF THE INVENTION

1. Field of the Invention

The present invention relates to new camptothecin derivatives useful as medicaments or intermediates therefor and a process for preparing the new camptothecin derivatives. More particularly, the present invention relates to new camptothecin derivatives carrying, in addition to a lower alkyl group in 7-position thereof, one or more substituents in 9-, 10-, 11- and/or 12-position thereof which are useful as anti-tumor drugs or intermediates therefor as well as a process for preparing the new camptothecin derivatives wherein 1,5-dioxo(5'-ethyl-2'H,5'H,6'H-6-oxopyrano) [3',4'-f]-Δ6(8)tetrahydroindolidine is condensed with an o-acyl-aniline compound (or more specifically, a lower alkanophenone carrying an amino group in 2-position of its phenyl group and one or more substituents in 3-, 4-, 5- and/or 6-position thereof) and the resultant corresponding 20-deoxycamptothecin derivative is oxidized.

2. Description of the Prior Art

Camptothecin represented by the following structural formula:

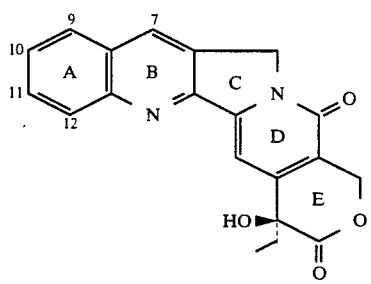

is an alkaloid extracted and isolated from *Camptotheca accuminata* (Nyssaceae), etc., which has a pentacyclic structure consisting of a characteristic fused 5-ring system consisting of quinoline (rings A and B), pyrroline (ring C), α-pyridone (ring D) and a six-membered lactone (ring E) and is distinguished by displaying a strong inhibitory activity toward biosynthesis of nucleic acid. In addition, camptothecin is a unique anti-tumor substance characterized by its rapid and reversible action, its lack of any cross-tolerance with the existing anti-tumor agents and by exhibiting a strong anti-tumor activity against experimentally transplanted carcinoma such as leukemia L-1210 in mice or Walker 256 tumor in rats. Although camptothecin is still regarded as one of the most potent substances possessing anti-tumor activity, the use of this compound itself for clinical treatments is significantly limited because of high toxicity. Moreover, camptothecin and the majority of derivatives thereof involve a problem of poor solubility in case of administration as medicaments.

For these reasons, a number of studies have been made heretofore not only to reduce toxicity of camptothecin while maintaining its anti-tumor activity by converting camptothecin chemically into its derivatives but also to make improvement in solubility of camptothecin and derivatives thereof by chemical modification of the camptothecin molecule or substituents therein. However, any chemical modification of the ring D and/or E of camptothecin, including ring-opening reactions of the ring D and/or E, revealed only failure in maintaining anti-tumor activity and very poor improvement in toxicity [J. Med. Chem., 19 (1976), 675]. From the chemotherapeutic point of view, therefore, it is of importance that the chemical modifications of camptothecin should be restricted in rings A, B and C without effecting any change in the rings D and E which are believed to be the essential structural elements for the expression of the above mentioned characteristic biological activities.

The present inventors made extensive researches for developing new class of camptothecin derivatives with co-workers on the basis of the above mentioned knowledge and found a process for preparing 5- and 7-substituted camptothecin derivatives (U.S. Pat. No. 4,399,282), a process for preparing various derivatives from these 5-and 7-substituted camptothecin derivatives (U.S. Pat. Nos. 4,399,276 and 4,399,282), a process for preparing 10- substituted camptothecin derivatives (U.S. Pat. Nos. 4,473,692 and 4,545,880), a process for preparing camptothecin derivatives disubstituted in 7-position and 9-, 10- or 11-position (U.S. Pat. No. 4,604,463) and a process for preparing 5- and/or 7-substituted camptothecin N-oxide derivatives (U.S. Pat. No. 4,513,138).

It was made clear from the studies on the various camptothecin derivatives prepared heretofore that introduction of an alkyl group into the 7-position of camptothecin tends to enhance anti-tumor activity. It is also noted that all of the camptothecin derivatives disclosed in these prior art references are derived from camptothecin or its derivatives but are not synthesized from other compounds which are not in possession of the fundamental structure of camptothecin.

For further extensive research based on these facts for sounding possibility of developing other new camptothecin derivatives also useful as anti-tumor agents or intermediates therefor and finding a new route for synthesizing camptothecin derivatives, there is still a great demand in the art for developing further new class of camptothecin derivatives carrying an alkyl group in 7-position thereof and various substituents in the ring A thereof according to a process quite different from the processes disclosed in the prior art references above mentioned.

BRIEF SUMMARY OF THE INVENTION

Accordingly, it is an object of the present invention to provide new camptothecin derivatives carrying, in addition to an alkyl group in 7-position thereof, one or more substituents in 9-, 10-, 11- and/or 12-position on the ring A thereof.

It is another object of the present invention to provide new camptothecin derivatives possessing strong anti-tumor activity with extremely weak toxicity.

It is still another object of the present invention to provide a process for the preparation of new camptothecin derivatives carrying, an alkyl group in 7-position thereof, one or more substituents in 9-, 10-, 11- and/or 12-position on the ring A thereof according to a simple and economical procedure.

It is further object of the present invention to provide a new means for synthesizing compounds having the fundamental structure of camptothecin from a starting material different from camptothecin.

Other objects, features and advantages of the present invention will become apparent more fully from the following description.

As a result of extensive researches made by the present inventors, it has now been found that new camptothecin derivatives carrying, in addition to an alkyl group in 7-position thereof, one or more substituents in 9-, 10-, 11- and/or 12-position on the ring A thereof are also strong in anti-tumor activity and can be synthesized totally from 1,5-dioxo(5'-ethyl-2'H,5'H,6'H-6-oxopyrano)[3',4'-f]-Δ6(8)-tetrahydroindolidine and an o-acyl-ananiline compound. The present invention has been accomplished on the basis of the above finding.

DETAILED DESCRIPTION OF THE INVENTION

In accordance with the present invention, there are provided new camptothecin derivatives represented by the general formula:

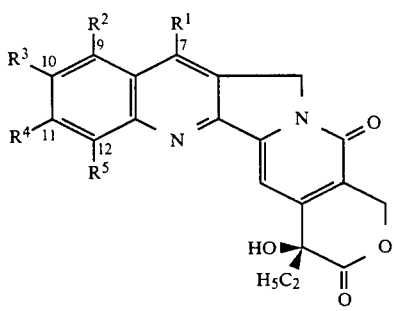 (I)

wherein $R^1$ represents a lower alkyl group, $R^2$ represents a hydrogen atom or an amino, hydroxyl, lower acylamino or lower alkoxy group, $R^3$ represents a hydrogen or halogen atom or a lower alkyl, hydroxyl, lower alkoxy, nitro, amino, cyano or di(lower alkyl)amino group, $R^4$ represents a hydrogen or halogen atom or a lower alkyl, hydroxyl, lower alkoxy, lower alkylthio, amino, cyano or di(lower alkyl)amino group, and $R^5$ represents a hydrogen or halogen atom of a hydroxyl or lower alkoxy group, with the proviso that all of the $R^2$, $R^3$, $R^4$ and $R^5$ substituents should not be a hydrogen atom and also that if any one of the $R^2$, $R^3$, $R^4$ and $R^5$ is a hydroxyl or lower alkoxy group, all of the other three substituents should not be a hydrogen atom.

In accordance with the present invention, there is also provided a process for the preparation of new camptothecin derivatives of the general formula (I) which comprises condensing 1,5-dioxo(5'-ethyl-2'H,5'H,6'H,-6-oxopyrano)[3',4'-f]-Δ6(8)-tetrahydroindolidine of the formula:

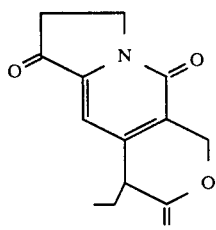 (II)

with an o-acyl-aniline compound of the general formula:

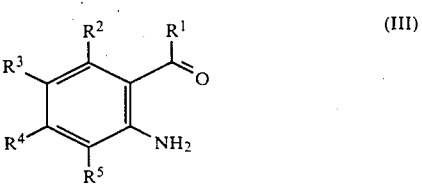 (III)

wherein $R^1$, $R^2$, $R^3$, $R^4$ and $R^5$ have the same meanings as given above, and oxidizing the resultant 20-deoxy-camptothecin derivative of the general formula:

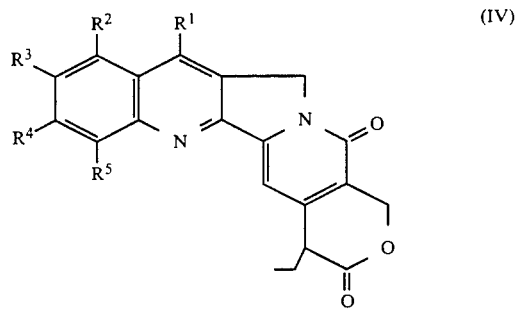 (IV)

wherein $R^1$, $R^2$, $R^3$, $R^4$ and $R^5$ have the same meanings as given above, with oxygen in the presence of cupric ion, and if desired, converting in the resultant camptothecin derivative of the general formula (I) any alkoxy group into the free hydroxyl group and any free amino group into a lower acylamino group.

The present invention is featured by providing new camptothecin derivatives carrying a lower alkyl group in 7-position thereof and at least one substituent in 9-, 10-, 11- and/or 12-position on the fused benzene ring A with the proviso that any one of the substituents is a hydroxyl or lower alkoxy group, at least one of the other substituents should be one other than hydrogen atom. The present invention is also featured by preparing the camptothecin derivatives without chemical modifications of the starting compound having the skeleton of camptothecin.

In the new camptothecin derivatives of the general formula (I), the starting o-acyl-aniline compounds of the general formula (III) and the 20-deoxy intermediate of the general formula (IV), the term "a lower alkyl group" means an alkyl group with 1-8, preferably 1-4 carbon atoms. The alkyl group has generally a straight chain but may be branched at any position if the alkyl group has at least 3 carbon atoms. Illustrative of the lower alkyl group are, for example, methyl, ethyl, propyl, isopropyl, tert-butyl, pentyl, hexyl, heptyl and octyl. Preferable are methyl, ethyl, propyl, isopropyl and butyl. This definition also applies to a lower alkyl moiety in the lower alkoxy, alkylthio and di(lower alkyl)amino groups. Accordingly, the lower alkoxy group, for example, has 1-8, preferably 1-4 carbon atoms in its alkyl moiety which may have a straight or branched chain. Likewise, the lower acyl group has 1-8, preferably 1-4 carbon atoms in its molecule, typical examples of which include acetyl, propionyl, butyryl, pentanoyl, hexanoyl and octanoyl. The halogen atom is an important substituent and is selected normally from fluorine, chlorine and bromine atoms.

In case at least one substituent on the benzene ring A of the camptothecin derivatives is a lower alkyl group, this group may be same as or different from the lower alkyl group $R^1$ located in 7-position of the camptothecin derivatives. In case plural substituents of the same kind exist, they may be same or different. For example, when $R^2$ and $R^3$ are halogen atoms, they may be the same or different.

Among the new camptothecin derivatives of this invention represented by the general formula (I), some are extremely strong in anti-tumor activity and so can be used as anti-tumor drugs while some are not so strong in anti-tumor activity but can be used as intermediates for preparing anti-tumor drugs. Illustrative of the new camptothecin derivatives of this invention are, for example, 7-methyl-10-fluoro-camptothecin (for brevity, the term "camptothecin" will be referred to in this sentence simply as CPT), 7-methyl-10-chloro-CPT, 7-methyl-10-bromo-CPT, 7-methyl-11-fluoro-CPT, 7-methyl-11-chloro-CPT, 7-methyl-11-bromo-CPT, 7-methyl-12-fluoro-CPT, 7-methyl-12-chloro-CPT, 7-methyl-12-bromo-CPT, 7-methyl-9,10-dimethoxy (or -dihydroxy)-CPT, 7-methyl-9,12-dimethoxy(or -dihydroxy)-CPT, 7-methyl-10,11-dimethoxy(or -dihydroxy)-CPT, 7-methyl-9-hydroxy-12-methoxy-CPT, 7-methyl-9,10,11-trimethoxy-CPT, 7-methoxy-9-amino-CPT, 7methoxy-9-acetoamino-CPT, 7-methyl-10-amino-CPT, 7methyl-10-dimethylamino-CPT, 7-methyl-11-amino-CPT, 7,10-dimethyl-CPT, 7-methyl-11ethyl-CPT, 7-methyl-10cyano-CPT, 7-methyl-10-nitro-CPT, 7-methyl-11-methylthio-CPT, and the corresponding 7-ethyl-, 7-propyl-, 7-isopropyl- and 7-butyl-analogues.

According to the process of this invention, the new camptothecin derivative of the general formula (I) can be prepared according to the following reaction scheme:

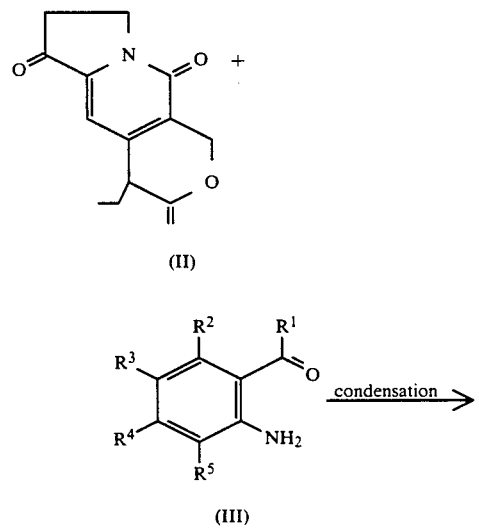

(II)

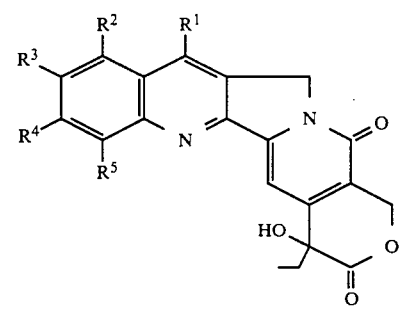

(III)

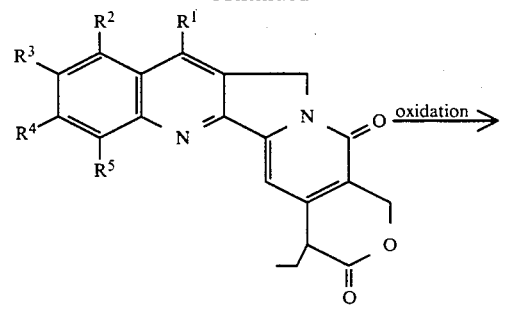

(IV)

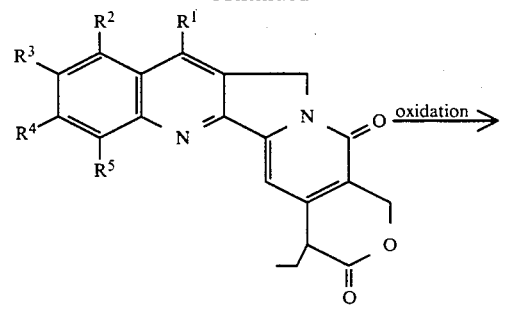

(I)

The reactions themselves (Friedländer's condensation followed by oxidation) adopted in the process of this invention are known in this art. The compound of the formula (II), i.e. 1,5-dioxo(5'-ethyl-2'H,5'H,6'H-6-oxopyrano)[3',4'-f]-Δ6(8)-tetrahydroindolidine, is known and can be prepared according to the method disclosed in M. C. Wani et al., J. Med. Chem., 23, 554 (1980). The majority of the o-acyl-aniline compounds (or more specifically, a lower alkano phenone carrying an amino group in 2-position of its benzene ring and one or more substituents in 3-, 4-, 5- and/or 6-position thereof) is known and commercially available. However, the compounds of the general formula (II) can be prepared at need according to the methods known per se.

The condensation reaction of the compound of the formula (II) with the compound of the general formula (III) is carried out under the conditions customarily used in Friedländer's reaction. Thus, the reactants are dissolved in a solvent inert to the reaction and heated under reflux in the presence of a dehydration catalyst. As the reaction itself is a dehydro-condensation reaction, the solvent utilizable therefor is preferably an aromatic hydrocarbon which forms a heterogenous phase to water and can be distilled with water, forming an azeotrope. Preferable examples of the aromatic hydrocarbon include benzene, toluene and xylene which are used singly or as a mixture, considering the relation between the reaction temperature and their boiling points. It is preferable to use a Dean-Stark apparatus to facilitate separation of water formed during the condensation reaction. The time required for the reaction varies according to the reactants but is usually from 8 hours to 2 days. After completion of the reaction, the solvent is removed from the reaction mixture preferably under reduced pressure and the residue is washed with a solvent such as chloroform-ether. The condensation product thus obtained, i.e. the corresponding 20-deoxy camptothecin derivative of the general formula (IV) is usually used as such for the subsequent step without necessity of purification.

A preferable example of the dehydration catalyst used in this case is p-toluenesulfonic acid. The reaction temperature is generally maintained above the boiling point of water or its azeotrope with the inert solvent.

The 20-deoxy camptothecin derivative of the general formula (IV) is then oxidized to the derivative of the general formula (I). For this, the 20-deoxy derivative is dissolved in a solvent inert to the reaction. A preferable solvent for this purpose is dimethylformamide, diethylformamide or dimethylsulfoxide. A cupric salt such as cupric chloride, cupric acetate or cupric nitrate in a proper amount is then dissolved in the solution and gaseous oxygen is blown into the mixture until the starting 20-deoxy derivative is completely oxidized. After completion of the reaction, the solvent used is removed by distillation and the residual product is subjected to purification by way of thin layer or column chromatography using chloroform-methanol as eluent.

The substituents in the camptothecin derivatives of the general formula (I) thus obtained may be converted, if desired, into other substituents. For example, the lower alkoxy group or groups can be converted completed or partially into the free hydroxyl group by heating the lower alkoxy derivative under reflux in a solvent inert to the reaction, such as 1,1,2,2-tetrachloroethane, toluene or benzene in the presence of aluminum salt such as aluminum chloride or aluminum bromide. Alternatively, the lower alkoxy derivatives may be boiled with a concentrated hydrohalic acid such as 48% hydrobromic acid for several hours to effect solvolysis.

The camptothecin derivatives carrying a free amino group as substituent can be treated with an acylating agent to convert their free amino group into the corresponding acylamino group. For this, the camptothecin derivatives carrying the free amino group is dissolved in a solvent inert to the reaction and is reacted with 3-5 equivalents of an acylating agent in the presence of a tertiary amine as a base at a temperature ranging from ice-cooling temperature to room temperature. Illustrative of the solvent utilizable for this acylation are, for example, methylene chloride, chloroform, dioxane, tetrahydrofuran, acetonitrile and dimethylsulfoxide. Utilizable as the tertiary amine are, for example, triethylamine, pyridine, picoline and pyrrolidine. A lower alkanoic halide such as acetyl chloride or a lower alkanoic anhydride such as acetic anhydride can be used as the acylating agent.

The o-acyl-aniline compound of the general formula (III) as one of the reactants for the condensation reaction may be prepared, for example, according to a process as disclosed in T. Sugasawa, T. Toyoda, M. Adachi and K. Sasakura, J. Am. Chem. Soc., 100, 4842 (1978) and as shown in the following reaction scheme:

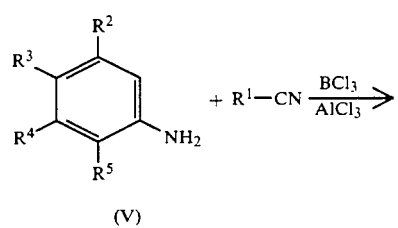

(V)

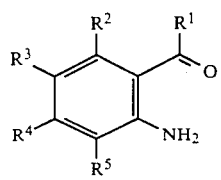

(III)

Thus, 1.1 equivalent of boron trichloride is dissolved in an inert solvent such as benzene, toluene, dichloroethane or tetrachloroethane, preferably benzene, and 1 equivalent of an aniline derivative (V) is added with ice-cooling. To the resultant aniline-boron trichloride adduct is added 1 to 2 equivalents of a nitrile (R-CN: lower alkyl- or branched lower alkylnitrile), and 1.1 equivalent of aluminum chloride is then added. The mixture is heated under reflux for 8 to 20 hours and then ice-cooled. After addition of 2N-hydrochloric acid, the mixture is stirred at 80° C. for one hour. After cooling, water is added to the reaction mixture.

In case the end product exists in the organic phase, the organic phase is separated and the aqueous phase is further extracted with an organic solvent such as benzene or ethyl acetate. The extract and the organic phase are combined and washed with water.

Where the product is in the aqueous phase, the organic phase is discarded, and the aqueous phase is further washed with an organic solvent such as benzene or ethyl acetate. The aqueous phase is made alkaline with an aqueous solution of a caustic alkali, extracted several times with an organic solvent as mentioned above, and washed with water.

The organic phase obtained in either case is then dried with a drying agent such as anhydrous sodium sulfate or anhydrous magnesium sulfate, and the solvent is distilled off under reduced pressure. The residue is recrystallized from an appropriate solvent such as n-hexane, chloroform-n-hexane or ether, or is first separated and purified by column chromatography on silica gel (eluent : toluene-ethyl acetate system, chloroform-n-hexane system, benzene-n-hexane system) and then crystallized from an appropriate solvent.

Cyano-substituted derivatives can be prepared by reacting a corresponding bromo-substituted derivative dissolved in a solvent inert to the reaction such as dimethylformamide with cuprous cyanide under heat in nitrogen atmosphere, according to the following reaction scheme:

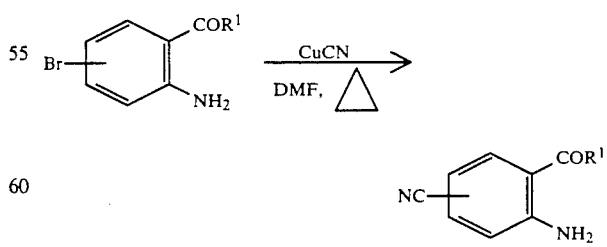

Accordingly, selection of the substituents $R^1$-$R^5$ in the camptothecin derivatives can advantageously be made at the stage of preparing the compound of the general formula (III) although some substituents (e.g. alkoxy or amino group) may optionally be converted into other substituents even after the main condensation reaction.

The anti-tumor activity of the camptothecin derivatives of the present invention can be demonstrated by the following Experiments wherein the camptothecin derivatives of this invention were subjected together with similar comparative compounds to screening with KB and L1210 cells. The results are shown below.

METHODS

The cells used for the experiments were KB cells, i.e. cultured cell strain derived from human nasopharyngeal cancer, and mouse leukemia-derived L1210 cells (Dainippon Pharmaceutical, Japan) both being kept freezed. KB cells were cultured in Eagle's minimal essential medium (Nissui Pharmaceutical, Japan) with 10% calf serum (GIBCO Laboratories and L1210 cells were cultured in RPMI 1640 medium (Nissui Pharmaceutical) with 10% fetal bovine serum (GIBCO Laboratories). Both cells were cultured at 37° C. in carbon dioxide gas incubator (5% $CO_2$).

The cell growth-inhibitor test with the drugs was carried out in the following manner based on the random screening method by Cancer Chemotherapy Center, Japanese Foundation for Cancer Research [Report of Special Committee on anticancer agents screening, Special Cancer Research Administration Group (Gan-Tokubetsu-Kenkyu Sokatsu-Han), Ministry of Education, Jpn. J. Cancer Chemother., 11(9), Part II: p1905, 1984]. In the case of KB cells, the cells were diluted to give a $2 \times 10^4$/ml culture on day 1. 3 Ml of the culture was placed in a 60 mm plastic Petri dish. On day 0, the medium was replaced with culture medium containing each camptothecin derivative in an appropriate concentration and the cells were incubated for additional 3 days. On day 3, the cells were detached from the Petri dish with 0.25% trypsin (GIBCO Laboratories) and the cells were counted with a Coulter Counter (Type ZM, Coulter Electronics). In the case of L1210 cells, the cells were diluted to give a $4 \times 10^4$/ml culture on day 0. 0.5 Ml portion of the culture was placed in each well of a 24-well plate, and pre-cultured for 3 hours. 0.5 Ml of culture medium containing each camptothecin derivative in an appropriate concentration was added thereto and incubated for 3 days, and the cells were counted on day 3 with the Coulter counter.

The growth-inhibitor rate was calculated by subtracting the number of treated cells from the number of untreated control cells to give the genuine growth-inhibition rate. The 50% effective dose ($ED_{50}$) was calculated from the obtained growth-inhibition curve by interpolation. The camptothecin derivatives were respectively dissolved in dimethylsulfoxide (DMSO) at a concentration of 1 mg/ml and kept at $-20°$ C. Under this condition, the effect of DMSO on $ED_{50}$ was not observed.

RESULTS

| Camptothecin derivatives tested (with $R^1$-$R^4$ in the formula indicated) | KB cells $ED_{50}$ (ng/ml) | L1210 cells $ED_{50}$ (ng/ml) |
|---|---|---|
| Experiment 1 | | |
| $R^1$ = Me $R^4$ = Br | 0.44 | 1.2 |
| $R^1$ = Et $R^3$ = Me | 0.46 | 1.4 |
| Camptothecin | 1.6 | 5.0 |
| 7-ethyl-10-hydroxy-camptothecin | 0.52 | 3.9 |
| Experiment 2 | | |
| $R^1$ = Et $R^3$ = Br | 0.42 | 1.0 |
| $R^1$ = Et $R^3$ = Cl | 0.35 | 1.1 |
| $R^1$ = Et $R^3$ = F | 1.0 | 2.2 |
| $R^1$ = Et $R^4$ = Br | 1.1 | 1.8 |
| $R^1$ = Et $R^4$ = Cl | 0.48 | 1.1 |
| $R^1$ = Et $R^4$ = F | 0.17 | 0.43 |
| Camptothecin | 1.3 | 1.6 |
| 7-ethyl-10-hydroxy-camptothecin | 0.47 | 3.2 |
| Experiment 3 | | |
| $R^1$ = Pr $R^3$ = Me | 1.2 | 1.9 |
| $R^1$ = Pr $R^4$ = Cl | 0.62 | 1.5 |
| $R^1$ = Bu $R^3$ = Br | 1.1 | 1.5 |
| Camptothecin | 1.5 | 4.7 |
| 7-ethyl-10-hydroxy-camptothecin | 0.48 | 3.4 |
| Experiment 4 | | |
| $R^1$ = Et $R^3$ = $R^4$ = Cl | 0.54 | 0.61 |
| Camptothecin | 1.5 | 4.1 |
| 7-ethyl-10-hydroxy-camptothecin | 0.51 | 2.4 |
| Experiment 5 | | |
| $R^1$ = Et $R^3$ = $NH_2$ | 0.26 | 1.1 |
| Camptothecin | 1.5 | 4.8 |
| 7-ethyl-10-hydroxy-camptothecin | 0.47 | 3.6 |
| Experiment 6 | | |
| $R^1$ = Et $R^3$ = $OCH_3$ $R^4$ = F | 0.14 | 0.40 |
| $R^1$ = Et $R^3$ = OH $R^4$ = F | 0.31 | 2.2 |
| $R^1$ = Et $R^4$ = $CH_3NH_2.HCl$ | 0.42 | 2.3 |
| Camptothecin | 1.4 | 4.3 |
| 7-ethyl-10-hydroxy-camptothecin | 0.45 | 3.7 |
| Experiment 7 | | |
| $R^1$ = Et $R^3$ = $CH_3$ $R^4$ = F | 0.17 | 0.37 |
| $R^1$ = Et $R^3$ = $R^4$ = F | 0.31 | 0.55 |
| Camptothecin | 1.2 | 4.1 |
| 7-ethyl-10-hydroxy-camptothecin | 0.44 | 3.1 |

Examples of the preparation of novel camptothecin derivatives are given below together with data from analytical instruments.

EXAMPLE 1

7-Methyl-11-bromocamptothecin 1,5-Dioxo(5'-ethyl-2'H,5'H, 6'H-6-oxopyrano)[3',4'-f]-Δ6(8)tetrahydroindolidine (1.00 g, 4.06 mmol), 2-amino-4-bromoacetophenone (957 mg, 4.47 mmol) and p-toluenesulfonic acid (320 mg) are dissolved in 200 ml of toluene and boiled under reflux for 24 hours using a Dean-Stark apparatus. The solvent is distilled off under reduced pressure and the residue is washed with chloroform-ether, and then dissolved in 240 ml of dimethylformamide. 2.37 g of cupric chloride and 0.71 ml of 40% aqueous solution of dimethylamine are added to the solution, and oxygen gas is then blown into the mixture until the starting materials are no longer observed on the thin layer chromatogram. After completion of the reaction, the solvents are distilled off under reduced pressure, and the residue is subjected to isolation and purification by column chromatography on silica gel (chloroformmethanol system) whereby 1.02 g (55.4%) of the title compound is obtained.

M.P. 264–265° C. (with decomposition: referred to hereinafter as "d").

IR(KBr): 3397, 2965, 2925, 2865, 1750, 1656, 1596, 1156.

NMR (DMSO-d$_6$) δppm: 0.89 (3H, t, J=7.3Hz, 20-CH$_2$CH$_3$), 1.82–1.93 (2H, m, 20-CH$_2$CH$_3$) 2.75 (3H, s, 7-CH$_3$), 5.21 (2H, s, 5-CH$_2$-), 5.43 (2H, s, 17-CH$_2$-), 6.52 (1H, br.s, 20-OH), 7.30 (1H, s, 14-H), 7.80 (1H, dd, 10-H), 8.15 (1H, d, J$_{9,10}$=9.2 Hz, 9-H), 8.31 (1H, d, J$_{10,12}$=1.8 Hz, 12-H).

EXAMPLE 2

7-Methyl-12-fluorocamptothecin

Using 2-amino-3-fluoroacetophenone (see Preparation Example 21: 682 mg, 4.47 mmol), the reaction followed by the after-treatment is carried out in the same manner as in Example 1 whereby 0.65 g (42.2%) of the title compound is obtained.

MP 256–258.5° C. (d).

IR(KBr): 3379, 1757, 1657, 1621, 1150.

NMR (DMSO-d$_6$), δppm: 0.90 (3H, t, J=7.3 Hz, 20-CH$_2$CH$_3$), 1.83–1.94 (2H, m, 20-CH$_2$CH$_3$), 2.77 (3H, s, 7-CH$_3$), 5.24 (2H, s, 5-CH$_2$-), 5.43 (2H, s, 17-CH$_2$-), 6.54 (1H, br.s, 20-OH), 7.31 (1H, s, 14-H), 7.64–7.68 (2H, m 10 and 11-H), 8.00–8.03 (1H, m, 9-H).

EXAMPLE 3

7-Ethyl-9-aminocamptothecin

Using 2,6-diaminopropiophenone (see Preparative Example 20: 733 mg, 4.47 mmol) and p-toluenesulfonic acid (1.2 g), the reaction followed by the after-treatment is carried out in the same manner as in Example 1 whereby 0.32 g (20.5%) of the title compound is obtained.

MP 229–231° C. (d).

IR(KBr): 3360, 2958, 1744, 1650, 1592, 1160.

NMR(DMSO-d$_6$) δppm:

0.88 (3H, t, J=7.3 Hz, 20-CH$_2$CH$_3$), 1.36 (3H, t, J=7.7 Hz, 7-CH$_2$CH$_3$), 1.81–1.91 (2H, m, 20-CH$_2$CH$_3$), 3.31 (2H, q, 7-CH$_2$CH$_3$), 5.29 (2H, s, 5-CH$_2$), 5.42 (2H, s, 17-CH$_2$-), 6.48 (1H, s, 20-OH) 6.97 (1H, d, J$_{10,11}$=7.7 Hz, 10-H), 7.26 (1H, s, 14-H), 7.43 (1H, d, J$_{11,12}$=7.7 Hz, 12-H), 7.50 (1H, dd, 11-H).

EXAMPLE 4

7-Ethyl-9-acetaminocamptothecin 100 mg (0.26 mmol) of 7-ethyl-9-aminocamptothecin is suspended in 30 ml of methylene chloride. To the suspension are added 1 ml of triethylamine and 60 mg (0.76 mmol) of acetyl chloride in that order, and the mixture is stirred at room temperature for one day. The mixture is evaporated under reduced pressure to dryness and the residue is isolated and purified by column chromatography on silica gel (eluent: chloroform-methanol 50:1) and washed with ethanol whereby 10 mg (9.0%) of the title compound is obtained as pale yellow crystals.

MP 205°–210° C. (d).

IR(KBr): 3340, 2960, 2920, 1740, 1656, 1598, 1159.

NMR (DMSO-d$_6$) δppm: 0.89 (3H, t, J=7.3 Hz, 20-CH$_2$CH$_3$), 1.22 (3H, t, J=7.7 Hz, 7-CH$_2$CH$_3$), 1.83–1.93 (2H, m, 20-CH$_2$CH$_3$), 2.14 (3H, s, COCH$_3$), 3.28 (2H, q, 7-CH$_2$CH$_3$), 5.32 (2H, s, 5-CH$_2$-), 5.43 (2H, s, 17-CH$_2$-), 6.52 (1H, s, 20-OH), 7.32 (1H, s, 14-H), 7.49 (1H, d, J$_{10,11}$=7.7 Hz, 10-H), 7.81 (1H, dd, 11-H), 8.11 (1H, d, J$_{11,12}$=8.1 Hz, 12-H), 10.11 (1H, s, —NHCOCH$_3$).

EXAMPLE 5

7-Ethyl-10-fluoropropiophenone

Using 2-amino-5-fluoropropiophenone (see Preparative Example 8: 747 mg, 4.47 mmol), the reaction followed by the after-treatment is carried out in the same manner as in Example 1 whereby 0.92 g (57.3%) of the title compound is obtained.

MP 240°–242° C. (d).

IR(KBr): 3363, 2966, 1751, 1655, 1605, 1510, 1233, 1155.

NMR(DMSO-d$_6$)δppm: 0.89 (3H, t, J=7.3 Hz, 20-CH$_2$CH$_3$), 1.29 (3H, t, J=7.7 Hz, 7-CH$_2$CH$_3$), 1.79–1.95 (2H, m, 20-CH$_2$CH$_3$), 3.18 (2H, q, 7-CH$_2$CH$_3$), 5.29 (2H, s, 5-CH$_2$-), 5.43 (2H, s, 17-CH$_2$-), 6.51 (1H, s, 20-OH), 7.31 (1H, s, 14-H), 7.75 (1H, ddd, J$_{9,11}$=2.9 Hz, J$_{11,12}$=9.2 Hz, J$_{11,F}$=11.0 Hz, 11-H), 8.0 (1H, dd, J$_{9,F}$=10.6 Hz, 9-H), 8.21 (1H, dd, J$_{12,F}$=5.5 Hz, 12-H).

EXAMPLE 6

7-Ethyl-10-chlorocamptothecin

Using 2-amino-5-chloropropiophenone (see Preparative Example 9: 821 mg, 4.47 mmol), the reaction followed by the after-treatment is carried out in the same manner as in Example 1 whereby 0.70 g (42.1%) of the title compound is obtained.

MP 238°–239° C. (d).

IR(KBr): 3314, 2968, 1753, 1653, 1653, 1593.

NMR(DMSO-d$_6$)δppm: 0.88 (3H, t, J=7.3 Hz, 20-CH$_2$CH$_3$), 1.30 (3H, t, J=7.7 Hz, 7-CH$_2$CH$_3$), 1.78–1.97 (2H, m, 20-CH$_2$CH$_3$), 3.21 (2H, q, 7-CH$_2$CH$_3$), 5.30 (2H, s, 5-CH$_2$-), 5.43 (2H, s, 17-CH$_2$-), 6.52 (1H, s, 20-OH), 7.32 (1H, s, 14-H), 7.85 (1H, dd, J$_{9,11}$=2.2 Hz, J$_{11,12}$=9.2 Hz, 11-H), 8.16 (1H, d, 12-H), 8.31 (1H, d, 9-H).

EXAMPLE 7

7-Ethyl-10-bromocamptothecin

Using 2-amino-5-bromopropiophenone (see Preparative Example 10: 1.02 g, 4.47 mmol), the reaction followed by the after-treatment is carried out in the same manner as in Example 1 whereby 1.02 g (55.4%) of the title compound is obtained.

MP 241°–243° C. (d).

IR(KBr): 3500, 3340, 2967, 1736, 1654, 1608, 1451, 1149.

NMR (DMSO-d$_6$) δppm: 0.88 (3H, t, J=7.3 Hz, 20-CH$_2$CH$_3$), 1.30 (3H, t, J=7.7 Hz, 7-CH$_2$CH$_3$), 1.78–1.97 (2H, m, 20-CH$_2$CH$_3$), 3.21 (2H, q, 7-CH$_2$CH$_3$), 5.32 (2H, s, 5-CH$_2$-), 5.43 (2H, s, 17-CH$_2$-), 6.52 (1H, s, 20-OH), 7.33 (1H, s, 14-H), 7.96 (1H, dd, J$_{9,11}$=2.2 Hz, J$_{11,12}$=9.2 Hz, 11-H), 8.09 (1H, d, 12-H), 8.46 (1H, d, 9-H).

EXAMPLE 8

7-Ethyl-10-methylcamptothecin

Using 2-amino-5-methylpropiophenone (see Preparative Example 11: 728 mg, 4.47 mmol), the reaction followed by the after-treatment is carried out in the same manner as in Example 1 whereby 0.96 g (60.9%) of the title compound is obtained.

MP 245°–247° C. (d).

IR (KBr): 3400, 2965, 1751, 1651, 1590, 1157.

NMR (DMSO-d$_6$) δppm: 0.89 (3H, t, J=7.3 Hz, 20-CH$_2$CH$_3$), 1.31 (3H, t, J=7.7 Hz, 7-CH$_2$CH$_3$), 1.81–1.93 (2H, m, 20-CH$_2$CH$_3$), 2.58 (3H, s, 10-CH$_3$), 3.19 (2H, q, 7-CH$_2$CH$_3$), 5.28 (2H, s, 5-CH$_2$-), 5.43 (2H, s, 17-CH$_2$-), 6.50 (1H, s, 20-OH), 7.30 (1H, s, 14-H), 7.68 (1H, dd, J$_{9,11}$=1.8 Hz, J$_{11,12}$=8.5 Hz, 11-H), 8.03 (1H, d, 9-H), 8.05 (1H, d, 12-H).

EXAMPLE 9

7-Ethyl-10-cyanocamptothecin

Using 2-amino-5-cyanopropionphenone (see Preparative Example 31: 779 mg, 4.47 mmol), the reaction followed by the after-treatment is carried out in the same manner as in Example 1 whereby 0.51 g (31.1%) of the title compound is obtained.

MP 234°–237° C. (d).

IR(KBr): 3410, 2220, 1744, 1657, 1601, 1154.

NMR(DMSO-d$_6$) δppm: 0.88 (3H, t, J=7.3 Hz, 20-CH$_2$CH$_3$), 1.31 (3H, t, J=7.7 Hz, 7-CH$_2$CH$_3$), 1.79–1.96 (2H, m, 20-CH$_2$CH$_3$), 3.25 (2H, q, 7-CH$_2$CH$_3$), 5.36 (2H, s, 5-CH$_2$-), 5.44 (2H, s, 17-CH$_2$-), 6.55 (1H, s, 20-OH), 7.35 (1H, s, 14-H), 8.00 (1H, dd, J$_{9,11}$=1.8 Hz, J$_{11,12}$=8.8 Hz, 11-H), 8.45 (1H, d, 12-H), 8.70 (1H, d, 9-H).

EXAMPLE 10

7-Ethyl-10-nitrocamptothecin

Using 2-amino-5-nitropropiophenone (see Preparative Example 29: 894 mg, 4.47 mmol), the reaction followed by the after-treatment is carried out in the same manner as in Example 1 whereby 0.18 g (10.4%) of the title compound is obtained.

MP>360° C.

IR(KBr): 3415, 1750, 1652, 1598, 1340.

NMR(DMSO-d$_6$) δppm: 0.88 (3H, t, J=7.3 Hz, 20-CH$_2$CH$_3$), 1.35 (3H, t, J=8.1 Hz, 7-CH$_2$CH$_3$), 1.82–1.94 (2H, m, 20-CH$_2$CH$_3$), 3.33 (2H, q, 7-CH$_2$CH$_3$), 5.38 (2H, s, 5-CH$_2$-), 5.45 (2H, s, 17-CH$_2$-), 6.55 (1H, s, 20-OH), 7.39 (1H, s, 14-H), 8.35 (1H, d, J$_{11,12}$=9.5 Hz, 12-H), 8.53 (1H, dd, 11-H), 9.08 (1H, d, J$_{9,11}$=2.9 Hz, 9-H).

EXAMPLE 11

7-Ethyl-10-aminocamptothecin

Using 2,5-diaminopropiophenone (734 mg, 4.47 mmol) and p-toluenesulfonic acid (1.2 g), the reaction followed by the after-treatment is carried out in the same manner as in Example 1 whereby 0.22 g (14.1%) of the title compound is obtained.

MP 215°–217° C. (d).

IR(KBr): 3410, 3330, 2960, 1740, 1646, 1632, 1580, 1570, 1512, 1164.

NMR(DMSO-d$_6$) δppm: 0.88 (3H, t, J=7.3 Hz, 20-CH$_2$CH$_3$), 1.29 (3H, t, J=8.1 Hz, 7-CH$_2$CH$_3$), 1.79–1.91 (2H, m, 20-CH$_2$CH$_3$), 3.01 (2H, q, 7-CH$_2$CH$_3$), 5.22 (2H, s, 5-CH$_2$-), 5.40 (2H, d, J$_{gem}$=2.9 Hz, 17-CH$_2$-), 5.93 (2H, s, 10-NH$_2$), 6.44 (1H, s, 20-OH), 7.07 (1H, d, J$_{9,11}$=2.9 Hz, 9-H), 7.18 (1H, s, 14-H), 7.24 (1H, dd, 11-H), 7.84 (1H, d, J$_{11,12}$=8.8 Hz), 12-H).

EXAMPLE 12

7-Ethyl-10-dimethylaminocamptothecin

Using 2-amino-5-dimethylaminopropiophenone (see Preparative Example 19: 858 mg, 4.47 mmol) and p-toluenesulfonic acid (1.2 g), the reaction followed by the after-treatment is carried out in the same manner as in Example 1 whereby 0.59 g (34.9%) of the title compound is obtained.

MP 270°–271.5° C. (d).

IR(KBr): 3390, 2960, 1740, 1646, 1618, 1586, 1551, 1162.

NMR(DMSO-d$_6$) δppm: 0.88 (3H, t, J=7.0 Hz, 20-CH$_2$CH$_3$), 1.31 (3H, t, J=7.7 Hz, 7-CH$_2$CH$_3$), 1.81–1.92 (2H, m, 20-CH$_2$CH$_3$), 3.11 (8H, m, 10-N(CH$_3$)$_2$ and 7-CH$_2$CH$_3$), 5.22 (2H, s, 5-CH$_2$-), 5.41 (2H, d, J$_{gem}$=1.8 Hz, 17-CH$_2$-), 6.45 (1H, s, 20-OH), 6.96 (1H, d, J$_{9,11}$=2.6 Hz, 9-H), 7.20 (1H, s, 14-H), 7.53 (1H, dd, 11-H), 7.92 (1H, d, J$_{11,12}$=9.2 Hz, 12-H),

EXAMPLE 13

7-Ethyl-11-fluorocamptothecin

Using 2-amino-4-fluoropropiophenone (see Preparative Example 1: 747 mg, 4.47 mmol), the reaction followed by the after-treatment is carried out in the same manner as in Example 1 whereby 0.65 g (40.9%) of the title compound is obtained.

MP 196°–198° C. (d).

IR(KBr): 3335, 3080, 2960, 2920, 1746, 1652, 1597, 1509, 1214, 1154.

NMR(DMSO-d$_6$) δppm: 0.88 (3H, t, J=7.3 Hz, 20-CH$_2$CH$_3$), 1.32 (3H, t, J=7.7 Hz, 7-CH$_2$CH$_3$), 1.78–1.95 (2H, m, 20-CH$_2$CH$_3$), 3.23 (2H, q, 7-CH$_2$CH$_3$), 5.31 (2H, s, 5-CH$_2$-), 5.44 (2H, s, 17-CH$_2$-), 6.52 (1H, br.s, 20-OH), 7.33 (1H, s, 14-H), 7.65 (1H, ddd, J$_{9,10}$=9.2 Hz, J$_{10,12}$=2.9 Hz, J$_{10,F}$=11.4 Hz, 10-H), 7.90 (1H, dd, J$_{12,F}$=10.3 Hz, 12-H), 8.37 (1H, dd, J$_{9,F}$=5.9 Hz, 9-H).

EXAMPLE 14

7-Ethyl-11-chlorocamptothecin

Using 2-amino-4-chloropropionphenone (see Preparative Example 2: 821 mg, 4.47 mmol), the reaction followed by the after-treatment is carried out in the same manner as in Example 1 whereby 0.76 g (45.7%) of the title compound is obtained.

MP 205°–209° C. (d).

IR(KBr): 3375, 2965, 2920, 1745, 1654, 1602, 1155.

NMR(DMSO-d$_6$) δppm: 0.89 (3H, t, J=7.3 Hz, 20-CH$_2$CH$_3$), 1.31 (3H, t, J=7.7 Hz, 7-CH$_2$CH$_3$), 1.78–1.96 (2H, m, 20-CH$_2$CH$_3$), 3.22 (2H, q, 7-CH$_2$CH$_3$), 5.30 (2H, s, 5-CH$_2$-), 5.43 (2H, s, 17-CH$_2$-), 6.51 (1H, s, 20-OH), 7.32 (1H, s, 14-H), 7.72 (1H, dd, J$_{9,10}$=9.2 Hz, J$_{10,12}$=2.2 Hz, 10-H), 8.19 (1H, d, 12-H), 8.30 (1H, d, 9-H).

EXAMPLE 15

7-Ethyl-11-bromocamptothecin

Using 2-amino-4-bromopropiophenone (see Preparative Example 3: 1.02 g, 4.47 mmol), the reaction followed by the after-treatment is carried out in the same manner as in Example 1 whereby 0.75 g (40.5%) of the title compound is obtained.

MP 202°–204° C. (d).

IR(KBr): 3375, 2965, 2915, 1746, 1655, 1598, 1154.

NMR(DMSO-d$_6$) δppm: 0.88 (3H, t, J=7.3 Hz, 20-CH$_2$CH$_3$), 1.31 (3H, t, J=7.7 Hz, 7-CH$_2$CH$_3$), 1.79–1.94 (2H, m, 20-CH$_2$CH$_3$), 3.21 (2H, q, 7-CH$_2$CH$_3$), 5.30 (2H, s, 5-CH$_2$-), 5.44 (2H, s, 17-CH$_2$-), 6.52 (1H, s, 20-OH), 7.32 (1H, s, 14-H), 7.84 (1H, dd, J$_{9,10}$=9.2 Hz, J$_{10,12}$=2.2 Hz, 10-H), 8.23 (1H, d, 9-H), 8.36 (1H, d, 12-H).

EXAMPLE 16

7,11-Diethylcamptothecin

Using 2-amino-4-ethylpropiophenone (see Preparative Example 4: 791 mg, 4.47 mmol), the reaction followed by the after-treatment is carried out in the same manner as in Example 1 whereby 0.88 g (53.8%) of the title compound is obtained.

MP 224°–227° C. (d).

IR(KBr): 3400, 2965, 2920, 2875, 1752, 1652, 1590, 1159.

NMR(DMSO-$d_6$) $\delta$ppm: 0.89 (3H, t, J=7.3 Hz, 20-CH$_2$CH$_3$), 1.31 (3H, t, J=7.7 Hz, 11-CH$_2$CH$_3$), 1.33 (3H, t, J=7.7 Hz, 7-CH$_2$CH$_3$), 1.83–1.91 (2H, m, 20-CH$_2$CH$_3$), 2.87 (2H, q, 11-CH$_2$CH$_3$), 3.15 (2H, q, 7-CH$_2$CH$_3$), 5.30 (2H, s, 5-CH$_2$-), 5.43 (2H, s, 17-CH$_2$-), 6.51 (1H, s, 20-OH), 7.32 (1H, s, 14-H), 7.61 (1H, dd, $J_{9,10}$=8.8 Hz, $J_{10,12}$=1.8 Hz, 10-H), 7.97 (1H, d, 12-H), 8.20 (1H, d, 9-H).

EXAMPLE 17

7-Ethyl-11-methylthiocamptothecin

Using 2-amino-4-methylthiopropiophenone (see Preparative Example 6: 873 mg, 4.47 mmol), the reaction followed by the after-treatment is carried out in the same manner as in Example 1 whereby 0.92 g (53.6%) of the title compound is obtained.

MP 222°–225.5° C. (d).

IR(KBr): 3400, 2965, 2920, 1746, 1653, 1591, 1157.

NMR(DMSO-$d_6$) $\delta$ppm: 0.88 (3H, t, J=7.3 Hz, 20-CH$_2$CH$_3$), 1.30 (3H, t, J=7.7 Hz, 7-CH$_2$CH$_3$), 1.81–1.93 (2H, m, 20-CH$_2$CH$_3$), 2.65 (3H, s, 11-SCH$_3$), 3.18 (2H, q, 7-CH$_2$CH$_3$), 5.28 (2H, s, 5-CH$_2$-), 5.43 (2H, s, 17-CH$_2$-), 6.52 (1H, s, 20-OH), 7.30 (1H, s, 14-H), 7.56 (1H, dd, $J_{9,10}$=8.8 Hz, $J_{10,12}$=1.8 Hz, 10-H), 7.85 (1H, d, 12-H), 8.15 (1H, d, 9-H).

EXAMPLE 18

7-Ethyl-11-dimethylaminocamptothecin

Using 2-amino-4-dimethylaminopropiophenone (see Preparative Example: 858 mg, 4.47 mmol) and p-toluenesulfonic acid (1.2 g), the reaction followed by the after-treatment is carried out in the same manner as in Example 1, whereby 0.45 g (26.6%) of the title compound is obtained.

MP 211°–212° C. (d).

IR(KBr): 3405, 2955, 2915, 2865, 1751, 1652, 1622, 1601, 1152.

NMR(DMSO-$d_6$) $\delta$ppm: 0.88 (3H, t, J=7.3 Hz, 20-CH$_2$CH$_3$), 1.29 (3H, t, J=7.7 Hz, 7-CH$_2$CH$_3$), 1.80–1.92 (2H, m, 20-CH$_2$CH$_3$), 3.09 (7H, s, 11-N(CH$_3$)$_2$), 3.13 (2H, q, 7-CH$_2$CH$_3$), 5.20 (2H, s, 5-CH$_2$-), 5.42 (2H, s, 17-CH$_2$-), 6.47 (1H, s, 20-OH), 7.12 (1H, d, $J_{10,12}$=2.6 Hz, 12-H), 7.25 (1H, s, 14-H), 7.38 (1H, dd, 10-H), 8.05 (1H, d, $J_{9,10}$=9.5 Hz, 9-H).

EXAMPLE 19

7-Ethyl-11-cyanocamptothecin

Using 2-amino-4-cyanopropiophenone (see Preparative Example 30: 779 mg, 4.47 mmol), the reaction followed by the after-treatment is carried out in the same manner as in Example 1 whereby 0.47 g (28.9%) of the title compound is obtained.

MP 288°–292° C. (d).

IR(KBr): 3420, 2220, 1743, 1658, 1602, 1155.

NMR(DMSO-$d_6$) $\delta$pm: 0.88 (3H, t, J=7.3 Hz, 20-CH$_2$CH$_3$), 1.31 (3H, t, J=7.7 Hz, 7-CH$_2$CH$_3$), 1.79–1.96 (2H, m, 20-CH$_2$CH$_3$), 3.29 (2H, q, 7-CH$_2$CH), 5.34 (2H, s, 5-CH$_2$-), 5.44 (2H, s, 17-CH$_2$-), 6.54 (1H, s, 20-OH), 7.37 (1H, s, 14-H), 8.12 (1H, dd, $J_{9,10}$=8.8 Hz, $J_{10,12}$=1.8 Hz, 10-H), 8.28 (1H, d, 9-H), 8.92 (1H, d, 12-H).

EXAMPLE 20

7-Ethyl-11-aminocamptothecin

Using 2,4-diaminopropiophenone (see Preparative Example 20: 734 mg, 4.47 mmol) and p-toluenesulfonic acid (1.2 g), the reaction followed by the after-treatment is carried out in the same manner as in Example 1 whereby 0.12 g (7.7%) of the title compound is obtained.

MP 276°–279° C. (d).

IR(KBr): 3360, 2960, 2920, 1737, 1641, 1597, 1511, 1163.

NMR(DMSO-$d_6$) $\delta$ppm: 0.86 (3H, t, J=7.3 Hz, 20-CH$_2$CH$_3$), 1.27 (3H, t, J=7.7 Hz, 7-CH$_2$CH$_3$), 1.81–1.92 (2H, m, 20-CH$_2$CH$_3$), 3.07 (2H, q, 7-CH$_2$CH$_3$), 5.17 (2H, s, 5-CH$_2$-), 5.41 (2H, d, $J_{gem}$=3.3 Hz, 17-CH$_2$-), 5.92 (2H, s, 11-NH$_2$), 6.46 (1H, s, 20-OH), 7.04 (1H, d, $J_{10,12}$=2.2 Hz, 12-H), 7.11 (1H, dd, 10-H), 7.22 (1H, s, 14-H), 7.93 (1H, d, $J_{9,10}$=9.2 Hz, 9-H).

EXAMPLE 21

7-Ethyl-12-fluorocamptothecin

Using 2-amino-3-fluoropropiophenone (see Preparative Example 7: 746 mg, 4.47 mmol), the reaction followed by the after-treatment is carried out in the same manner as in Example 1 whereby 0.32 g (20.3%) of the title compound is obtained.

MP 244°–245° C. (d).

IR(KRr): 3400, 2960, 1755, 1654, 1605, 1148.

NMR(DMSO-$d_6$) $\delta$ppm: 0.89 (3H, t, J=7.3 Hz, 20-CH$_2$CH$_3$), 1.32 (3H, t, J=7.7 Hz, 7-CH$_2$CH$_3$), 1.82–1.94 (2H, m, 20-CH$_2$CH$_3$), 3.23 (2H, q, 7-CH$_2$CH$_3$), 5.34 (2H, s, 5-CH$_2$-), 5.44 (2H, s, 17-CH$_2$-), 6.54 (1H, s, 20-OH), 7.34 (1H, s, 14-H), 7.67–7.72 (2H, m, 10 and 11-H), 8.08–8.12 (1H, m, 9-H).

EXAMPLE 22

7-Ethyl-9,11-dimethoxycamptothecin

Using 2-amino-4,6-dimethoxypropiophenone (see Preparative Example 14: 934 mg, 4.47 mmol), the reaction followed by the after-treatment is carried out in the same manner as in Example 1 whereby 0.70 g 939.7%) of the title compound is obtained.

MP 242°–243° C. (d).

IR(KBr): 3380, 2970, 2920, 1752, 1653, 1619, 1596, 1453, 1267, 1237, 1207, 1160.

NMR(DMSO-$d_6$) $\delta$ppm: 0.88 (3H, t, J=7.3 Hz, 20-CH$_2$CH$_3$), 1.25 (3H, t, J=7.7 Hz, 7-CH$_2$CH$_3$), 1.76–1.96 (2H, m, 20-CH$_2$CH$_3$), 3.12–3.28 (2H, m, 7-CH$_2$CH$_3$), 3.92 (3H, s, 9 or 11-OCH$_3$), 3.95 (3H, s, 9 or 11-OCH$_3$), 5.10 (1H, d, $J_{gem}$=18.3 Hz, 5-CH(H)-), 5.16 (1H, d, 5-CH(H)-), 5.42 (2H, s, 17-CH$_2$-), 6.48 (1H, s, 20-OH), 6.71 (1H, d, $J_{10,12}$=2.6 Hz, 10-H), 7.10 (1H, d, 12-H), 7.23 (1H, s, 14-H).

EXAMPLE 23

7-Ethyl-9,11-dihydroxycamptothecin and 7-ethyl-11-hydroxy-9-methoxycamptothecin 7-Ethyl-9,11-dimethoxycamptothecin (600 mg, 1.37 mmol) is dissolved in 120 ml of 47% hydrobromic acid and the solution is boiled under reflux for 2.5 hours under a stream of nitrogen. The mixture is concentrated under reduced pressure to dryness, and the residue is isolated and purified by column chromatography on silica gel (eluent: chloroform-methanol system) and then recrystallized from ethanol whereby the title compounds, i.e. 341 mg (60.8%) of the 9,11-dihydroxy derivative and 10 mg (1.7%) of the 11-hydroxy-9-methoxy derivative, and obtained.

7-Ethyl-9,11-dihydroxycamptothecin

MP > 320° C.

IR(KBr): 3370, 3180, 2965, 1744, 1651, 1595, 1273, 1174, 1160.

NMR(DMSO-d$_6$) δppm: 0.87 (3H, t, J=7.3 Hz, 20-CH$_2$CH$_3$), 1.30 (3H, t, J=7.7 Hz, 7-CH$_2$CH$_3$), 1.78–1.95 (2H, m, 20-CH$_2$CH$_3$), 3.24–3.40 (2H, m, 7-CH$_2$CH$_3$), 5.20 (2H, s, 5-CH$_2$-), 5.42 (2H, s, 17-CH$_2$-), 6.49 (1H, s, 20-OH), 6.64 (1H, br. s, 10-H), 6.86 (1H, br. s, 12-H), 7.22 (1H, s, 14-H), 10.09 (1H, d, J=3.3 Hz, 9 or 11-OH), 10.54 (1H, d, J=3.3 Hz, 9 or 11-OH).

7-Ethyl-11-hydroxy-9-methoxycamptothecin

IR(KBr): 3380, 2965, 1737, 1652, 1598, 1383, 1269, 1239, 1153.

NMR(DMSO-d$_6$) δppm: 0.88 (3H, t, J=7.3 Hz, 20-CH$_2$CH$_3$), 1.27 (3H, t, J=7.3 Hz, 7-CH$_2$CH$_3$), 1.78–1.92 (2H, m 20-CH$_2$CH$_3$), 3.14–3.31 (2H, m, 7-CH$_2$CH$_3$), 3.95 (3H, s, 9-OCH$_3$), 5.17 (2H, s, 5-CH$_2$-), 5.42 (2H, s, 17-CH$_2$-), 6.49 (1H, s, 20-OH), 6.68 (1H, d, J$_{10,12}$=2.2 Hz, 10-H), 6.97 (1H, d, 12-H), 7.22 (1H, s, 14-H), 10.31 (1H, br. s, 11-OH).

EXAMPLE 24

7-Ethyl-9,12-dimethoxycamptothecin

Using 2-amino-3,6-dimethoxypropiophenone (see Preparative Example 15: 934 mg, 4.47 mmol), the reaction followed by the after-treatment is carried out in the same manner as in Example 1 whereby 0.91 g (51.6% of the title compound is obtained.

MP 241°–243° C. (d).

IR(KBr): 3370, 3200, 2920, 2825, 1754, 1660, 1615, 1558, 1463, 1266, 1240, 1143, 1108.

NMR(DMSO-d$_6$) δppm: 0.90 (3H, t, J=7.3 Hz, 20-CH$_3$), 1.26 (3H, t, J=7.3 Hz, 7-CH$_2$CH$_3$) 1.78–1.97 (2H, m, 20-CH$_2$CH$_3$), 3.27 (2H, q, 7-CH$_2$CH$_3$), 3.92 (3H, s, 9 or 12-OCH$_3$), 3.96 (3H, s, 9 or 12-OCH$_3$), 5.18 (1H, d, J$_{gem}$=18.7 Hz, 5-CH(H)-), 5.23 (1H, d, 5-CH(H)-) 5.43 (2H, s, 17-CH$_2$-), 6.54 (1H, s, 20-OH), 7.03 (1H, d, J$_{10,11}$=8.8 Hz, 11-H), 7.15 (1H, d, 10-H), 7.27 (1H, s, 14-H).

EXAMPLE 25

7-Ethyl-9,12-dihydroxycamptothecin

Using 7-ethyl-9,12-dimethoxycamptothecin (1.0 g, 2.29 mmol), the reaction followed by the after-treatment is carried out in the same manner as in Example 23 whereby 720 mg (76.9%) of the title compound is obtained.

MP 259°–260° C. (d).

IR(KRr): 3360, 2970, 1746, 1723, 1652, 1598, 1580, 1232, 1160.

NMR(DMSO-d$_6$) δppm: 0.89 (3H, t, J=7.3 Hz, 20-CH$_2$CH$_3$), 1.32 (3H, t, J=7.3 Hz, 7-CH$_2$CH$_3$), 1.78–1.97 (2H, m, 20-CH$_2$CH$_3$), 3.32–3.47 (2H, m, 7-CH$_2$CH$_3$), 5.29 (2H, s, 5-CH$_2$-), 5.41 (1H, d, J$_{gem}$=16.1 Hz, 17-CH(H)-), 5.45 (1H, d, 17-CH(H)-), 6.51 (1H, s, 20-OH), 6.89 (1H, dd, J$_{10,11}$=8.4 Hz, J$_{11,OH}$=2.6 Hz, 11-H), 6.98 (1H, dd, J$_{10,OH}$=2.2 Hz, 10-H), 7.58 (1H, s, 14-H), 9.07 (1H, d, 12-OH), 9.77 (1H, d, 9-OH).

EXAMPLE 26

7-Ethyl-10,11-dimethoxycamptothecin

Using 2-amino-4,5-dimethoxypropiophenone (see Preparative Example 16: 934 mg, 4.47 mmol), the reaction followed by the after-treatment is carried out in the same manner as in Example 1 whereby 0.63 g (35.9%), of the title compound is obtained.

MP 261°–263° C. (d).

IR(KRr): 3390, 3090, 2960, 1745, 1656, 1593, 1504, 1253, 1156.

NMR(DMSO-d$_6$) δppm: 0.88 (3H, t, J=7.3 Hz, 20-CH$_2$CH$_3$), 1.32 (3H, t, J=7.7 Hz, 7-CH$_2$CH$_3$), 1.77–1.95 (2H, m, 20-CH$_2$CH$_3$), 3.17 (2H, q, 7-CH$_2$CH$_3$), 3.97 (3H, s, 10 or 11-OCH$_3$), 4.00 (3H, s, 10 or 11-OCH$_3$), 5.25 (2H, s, 5-CH$_2$-), 5.42 (2H, s, 17-CH$_2$-), 6.39–6.55 (1H, br, 20-OH), 7.25 (1H, s, 14-H), 7.43 (1H, s, 9 or 12-H), 7.53 (1H, s, 9 or 12-H).

EXAMPLE 27

7-Ethyl-10,11-dihydroxycamptothecin and 7-ethyl-10-hydroxy-11-methoxycamptothecin Using 7-ethyl-10,11-dimethoxycamptothecin (1.0 g, 2.29 mmol), the reaction followed by the after-treatment is carried out in the same manner as in Example 23 whereby the title compounds, 356 mg (38.0%) of the 10,11-dihydroxy derivative and 38 mg (3.9%) of the 10-hydroxy-11-methoxy derivative, are obtained.

7-Ethyl-10,11-dihydroxycamptothecin

MP > 320° C.

IR(KBr); 3400, 2965, 1737, 1647, 1588, 1552, 1465, 1263, 1162.

NMR(DMSO-d$_6$) δppm:
0.88 (3H, t, J=7.3 Hz, 20-CH$_2$CH$_3$), 1.29 (3H, t, J=7.7 Hz, 7-CH$_2$CH$_3$), 1.78–1.94 (2H, m, 20-CH$_2$CH$_3$), 3.05 (2H, q, 7-CH$_2$CH$_3$), 5.22 (2H, s, 5-CH$_2$-), 5.41 (2H, s, 17-CH$_2$-), 6.20–6.76 (1H, br, 20-OH), 7.22 (1H, s, 14-H), 7.38 (1H, s, 9 or 12-H), 7.39 (1H, s, 9 or 12-H), 10.13 (1H, br.s, 10 or 11-OH), 10.38 (1H, br.s, 10 or 11-OH), 7-Ethyl-10-hydroxy-11-methoxycamptothecin MP 207°–210° C. (d).

IR(KBr): 3520, 3400, 2910, 1734, 1653, 1603, 1505, 1260, 1156.

NMR(DMSO-d$_6$) δppm:
0.88 (3H, t, J=7.3 Hz, 20-CH$_2$CH$_3$), 1.29 (3H, t, J=7.7 Hz, 7-CH$_2$CH$_3$), 1.78–1.93 (2H, m, 20-CH$_2$CH$_3$), 3.07 (2H, q, 7-CH$_2$CH$_3$), 3.99 (3H, s, 11-OCH$_3$), 5.25 (2H, s, 5-CH$_2$-), 5.39 (1H, d, J$_{gem}$=16.1 Hz, 17-CH(H)-), 5.44 (1H, d, 17-CH(H)-), 6.51 (1H, s, 20-OH), 7.26 (1H, s, 14-H), 7.42 (1H, s, 9-H), 7.53 (1H, s, 12-H), 10.23 (1H, br. s, 10-OH).

EXAMPLE 28

7-Ethyl-10,11-dichlorocamptothecin

Using 2-amino-4,5-dichloropropiophenone (see Preparative Example 13: 975 mg, 4.47 mmol), the reaction followed by the after-treatment is carried out in the same manner as in Example 1 whereby 0.72 g (40.0%) of the title compound is obtained.

MP 258°–262° C. (d).

IR(KRr): 3330, 3090, 2960, 2910, 1744, 1660, 1612, 1463, 1159.

NMR(DMSO-d$_6$) δppm: 0.88 (3H, t, J=7.3 Hz, 20-CH$_2$CH$_3$), 1.29 (3H, t, J=7.7 Hz, 7-CH$_2$CH$_3$), 1.78-1.97 (2H, m, 20-CH$_2$CH$_3$), 3.22 (2H, q, 7-CH$_2$CH$_3$), 5.31 (2H, s, 5-CH$_2$-), 5.44 (2H, s, 17-CH$_2$-), 6.53 (1H, s, 20-OH), 7.31 (1H, s, 14-H), 8.42 (1H, s, 9 or 12-H), 8.54 (1H, s, 9 or 12-H).

EXAMPLE 29

7-Ethyl-9,10,11-trimethoxycamptothecin

Using 2-amino-4,5,6-trimethoxypropiophenone (see Preparative Example 17: 1.07 g, 4.47 mmol), the reaction followed by the after-treatment is carried out in the same manner as in Example 1 whereby 0.85 g (50.5%) of the title compound is obtained.

MP 221°-223° C. (d).

IR(KRr): 3385, 2910, 1748, 1654, 1605, 1467, 1415, 1265, 1241, 1155, 1095, 1038.

NMR(DMSO-d$_6$) δppm: 0.88 (3H, t, J=7.3 Hz, 20-CH$_2$CH$_3$), 1.30 (3H, t, J=7.3 Hz, 7-CH$_2$CH$_3$), 1.77-1.98 (2H, m, 20-CH$_2$CH$_3$), 3.18-3.33 (2H, m, 7-CH$_2$CH$_3$), 3.90 (3H, s, 9, 10 or 11-OCH$_3$), 3.99 (3H, s, 9, 10 or 11-OCH$_3$), 4.00 (3H, s, 9, 10 or 11-OCH$_3$), 5.26 (2H, s, 5-CH$_2$-), 5.43 (2H, s, 17-CH$_2$-), 6.48 (1H, s, 20-OH), 7.26 (1H, s, 14-H), 7.44 (1H, s, 12-H).

EXAMPLE 30

7-Propyl-10-methylcamptothecin

Using 2-amino-5-methylbutyrophenone (see Preparative Example 25: 792 mg, 4.47 mmol), the reaction followed by the after-treatment is carried out in the same manner as in Example 1 whereby 1.02 g (62.1%) of the title compound is obtained.

MP 206°-208° C. (d).

IR(KRr): 3345, 2950, 2920, 2870, 1748, 1653, 1590, 1552, 1462, 1156.

NMR(DMSO-d$_6$) δppm: 0.89 (3H, t, J=7.3 Hz, 20-CH$_2$CH$_3$), 1.05 (3H, t, J=7.3 Hz, 7-CH$_2$CH$_2$CH$_3$), 1.72 (2H, tq, J=7.3 Hz, 7-CH$_2$CH$_2$CH$_3$), 1.78-1.95 (2H, m, 20-CH$_2$CH$_3$), 2.56 (3H, s, 10-CH$_3$), 3.21 (2H, t, J=7.3 Hz, 7-CH$_2$CH$_2$CH$_3$), 5.20 (2H, s, 5-CH$_2$-), 5.40 (1H, d, J$_{gem}$=16.5 Hz, 17-CH(H)-), 5.44 (1H, d, J$_{gem}$=16.5 Hz, 17-CH(H)-), 6.50 (1H, br.s, 20-OH), 7.29 (1H, s, 14-H), 7.56 (1H, dd, J$_{9,11}$=1.5 Hz, J$_{11,12}$=8.8 Hz, 11-H), 7.98 (1H, d, 9-H), 8.02 (1H, d, 12-H).

EXAMPLE 31

7-Propyl-11-chlorocamptothecin

Using 2-amino-4-chlorobutyrophenone (see Preparative Example 24: 803 mg, 4.47 mmol), the reaction followed by the after-treatment is carried out in the same manner as in Example 1 whereby 0.75 g (45.5%) of the title compound is obtained.

MP 150°-156° C. (d).

IR(KBr): 3400, 2955, 2920, 1748, 1655, 1604, 1155.

NMR(DMSO-d$_6$) δppm: 0.88 (3H, t, J=7.3 Hz, 20-CH$_2$CH$_3$), 1.04 (3H, t, J=7.3 Hz, 7-CH$_2$CH$_2$CH$_3$), 1.73 (2H, tq, J=7.3 Hz, 7-CH$_2$CH$_2$CH$_3$), 1.78-1.95 (2H, m, 20-CH$_2$CH$_3$), 3.18 (2H, t, J=7.3 Hz, 7-CH$_2$CH$_2$CH$_3$), 5.30 (2H, s, 5-CH$_2$-), 5.44 (2H, s, 17-CH$_2$-), 6.52 (1H, s, 20-OH), 7.33 (1H, s, 14-H), 7.73 (1H, dd, J$_{9,10}$=8.8 Hz, J$_{10,11}$=2.2 Hz, 10-H), 8.20 (1H, d, 12-H), 8.32 (1H, d, 9-H).

EXAMPLE 32

7-Butyl-10-bromocamptothecin

Using 2-amino-5-bromovalerophenone (see Preparative Example 28: 1.14 g, 4.47 mmol), the reaction followed by the after-treatment is carried out in the same manner as in Example 1 whereby 0.73 g (37.4%) of the title compound is obtained.

MP 223°-229° C. (d).

IR(KBr): 3350, 2945, 1745, 1654, 1598, 1456, 1161.

NMR(DMSO-d$_6$) δppm: 0.89 (3H, t, J=7.3 Hz, 20-CH$_2$CH$_3$), 0.96 (3H, t, J=7.3 Hz, 7-CH$_2$CH$_2$CH$_2$CH$_3$), 1.49 (2H, tq, J=7.3 Hz, 7-CH$_2$CH$_2$CH$_2$CH$_3$), 1.58-1.70 (2H, m, 7-CH$_2$CH$_2$CH$_2$CH$_3$), 1.78-1.96 (2H, m, 20-CH$_2$CH$_3$), 3.16 (2H, t, J=8.1 Hz, 7-CH$_2$CH$_2$CH$_2$CH$_3$), 5.26 (2H, s, 5-CH$_2$-), 5.43 (2H, s, 17-CH$_2$-), 6.51 (1H, s, 20-OH), 7.31 (1H, s, 14-H), 7.93 (1H, dd, J$_{9,11}$=2.2 Hz, J$_{11,12}$=9.2 Hz, 11-H), 8.06 (1H, d, 12-H), 8.40 (1H, d, 9-H).

EXAMPLE 33

7-Isopropyl-12-bromocamptothecin

Using 2-amino-3-bromoisobutyrophenone (see Preparative Example 26: 1.08 g, 4.47 mmol), the reaction followed by the after-treatment is carried out in the same manner as in Example 1 whereby 0.32 g (17.1%) of the title compound is obtained.

MP 268°-272° C. (d).

IR(KBr): 3500, 2965, 1727, 1655, 1606, 1553, 1152.

NMR(DMSO-d$_6$) δppm:

0.90 (3H, t, J=7.3 Hz, 20-CH$_2$CH$_3$), 1.49 (6H, d, J=5.9 Hz, 7-CH(CH$_3$)$_2$), 1.78-1.98 (2H, m, 20-CH$_2$CH$_3$), 3.96-4.12 (1Hm, m, 7-CH(CH$_3$)$_2$), 5.44 (4H, s, 5 and 17-CH$_2$-), 6.57 (1H, s, 20-OH), 7.37 (1H, s, 14-H), 7.60 (1H, dd, J=8.1 Hz, 10-H), 8.23 (1H, d, J=7.3 Hz, 9 or 10-H), 8.42 (1H, d, J=8.8 Hz, 9 or 10-H).

EXAMPLE 34

7-Ethyl-11-fluoro-10-methoxycamptothecin

Using 2-amino-4-fluoro-5-methoxypropiophenone (see Preparative Example 33: 882 mg, 4.47 mmol), the reaction followed by the after-treatment is carried out in the same manner as in Example 1 whereby 1.00 g (57.8%) of the title compound is obtained. It was recrystallized from chloroform-n-hexane. Colorless crystals.

MP 242°-244° C. (d).

IR(KBr)cm$^{-1}$: 3400, 1744, 1656, 1606, 1511, 1263, 1156.

NMR(DMSO-d$_6$) δppm: 0.88 (3H, t, J=7.3 Hz, 20-CH$_2$CH$_3$), 1.32 (3H, t, J=7.7 Hz, 7-CH$_2$CH$_3$), 1.75-1.97 (2H, m, 20-CH$_2$CH$_3$), 3.22 (2H, q, 7-CH$_2$CH$_3$), 4.08 (3H, s, —OCH$_3$), 5.29 (2H, s, 5-H$_2$), 5.43 (2H, s, 17-H$_2$), 6.50 (1H, s, 20-OH), 7.27 (1H, s, 14-H), 7.65 (1H, J$_{9,F}$=9.2 Hz, 9-H), 7.95 (1H, d, J$_{12,F}$=12.5 Hz, 12-H).

EXAMPLE 35

7-Ethyl-11-fluoro-10-hydroxycamptothecin

Using 7-ethyl-11-fluoro-10-methoxycamptothecin (1.7, 4.00 mmol), the reaction followed by the after-treatment is carried out in the same manner as in Example 23 whereby 1.39 g (84.5%) of the title compound is obtained.

MP 225°-228° C. (d).

NMR (DMSO-d$_6$) δ ppm: 0.87 (3H, t, J=7.3 Hz, 20-CH$_2$CH$_3$), 1.30 (3H, t, J=7.7 Hz, 7-CH$_2$CH$_3$), 1.76-1.95 (2H, m, 20-CH$_2$CH$_3$), 3.09 (2H, q, 7-CH$_2$CH$_3$), 5.28 (2H, s, 5-H$_2$), 5.42 (2H, s, 17-H$_2$), 7.26 (1H, s, 14-H), 7.60 (1H, d, J$_{9,F}$=9.5 Hz, 9-H), 7.91 (1H, d, J$_{12,F}$=12.1 Hz, 12-H), 10.64-11.10 (1H, br, 10-OH).

REFERENTIAL EXAMPLE 1

7-Methyl-10-ethoxycampothecin 1,5-Dioxo(5'-ethyl2'H,5'H,6'H-6-oxopyrano) [3',4'-f]-Δ6(8)-tetrahydroindolidine (1.00 g, 4.06 mmol), 2-amino-5-ethoxyacetophenone (800 mg, 4.47 mmol) and p-toluenesulfonic acid (320 mg) are dissolved in 200 ml of toluene and the solution is boiled under reflux for 24 hours using a Dean-Stark apparatus. The solvent is distilled off under reduced pressure and the residue is washed with chloroform-ether and then dissolved in 240 ml of dimethylformamide. 2.37 g of cupric chloride and 0.71 ml of 40% aqueous solution of dimethylamine are added to the solution, and oxygen gas is then blown into the mixture until the starting materials are no longer observed on the thin layer chromatogram. After completion of the reaction, the solvents are distilled off under reduced pressure, and the residue is subjected to isolation and purification by column chromatography on silica gel (chloroform-methanol system) whereby 0.58 g (58.3%) of the title compound, yellow in color, is obtained.

MP 243°–244° C. (d=decomposition).

IR(KBr): 3400, 2970, 2920, 1740, 1657, 1599, 1236, 1158.

NMR(DMSO-$d_6$) δ ppm: 0.89 (3H, t, J=7.3 Hz, 20-CH$_2$CH$_3$), 1.43 (3H, t, J=7.0 Hz, 10-OCH$_2$CH$_3$), 1.81–1.92 (2H, m, 20-CH$_2$CH$_3$), 2.71 (3H, s, 7-CH$_3$), 4.25 (2H, q, 10-OCH$_2$CH$_3$), 5.23 (2H, s, 5-CH$_2$—), 5.42 (2H, s, 17-CH$_2$—), 6.48 (1H, s, 20-OH), 7.26 (1H, s, 14-H), 7.42 (1H, d, $J_{9,11}$=2.9 Hz, 9-H), 7.48 (1H, dd, 11-H), 8.04 (1H, d, $J_{11,12}$=9.2 Hz, 12-H).

REFERENTIAL EXAMPLE 2

7-Ethyl-10-methylthiocamptothecin

Using 2-amino-5-methylthiopropiophenone (see Preparative Example 12: 873 mg, 4.47 mmol), the reaction followed by the after-treatment is carried out in the same manner as in Referential Example 1 whereby 1.07 g (62.6%) of the title compound is obtained.

MP 259°–261° C. (d).

IR(KBr): 3350, 2970, 2910, 1740, 1652, 1593, 1162.

NMR(DMSO-$d_6$) δ ppm: 0.93 (3H, t, J=7.3 Hz, 20-CH$_2$CH$_3$), 1.38 (3H, t, J=8.1 Hz, 7-CH$_2$CH$_3$), 1.83–1.94 (2H, m, 20-CH$_2$CH$_3$), 2.67 (3H, s, 10-SCH$_3$), 3.22 (2H, q, 7-CH$_2$CH$_3$), 5.28 (2H, s, 5-CH$_2$—), 5.34 (1H, d, $J_{gem}$=16.3 Hz, 17-CH(H)—), 5.49 (1H, d, 17-CH(H)—), 6.40 (1H, s, 20-OH), 7.38 (1H, s, 14-H), 7.68 (1H, dd, $J_{9,11}$=1.5 Hz, $J_{11,12}$=8.8 Hz, 11-H), 7.83 (1H, d, 9-H), 8.06 (1H, d, 12-H).

REFERENTIAL EXAMPLE 3

7-Ethyl-11-methoxycamptothecin

Using 2-amino-4-methoxypropiophenone (see Preparative Example 5: 802 mg, 4.47 mmol), the reaction followed by the after-treatment is carried out in the same manner as in Referential Example 1 whereby 1.01 g (61.4%) of the title compound is obtained.

MP 228°–230° C. (d).

IR(KBr): 3375, 2965, 2920, 1746, 1654, 1605, 1224, 1156.

NMR(DMSO-$d_6$) δ ppm: 0.88 (3H, t, J=7.3 Hz, 20-CH$_2$CH$_3$), 1.30 (3H, t, J=7.7 Hz, 7-CH$_2$CH$_3$), 1.78–1.96 (2H, m, 20-CH$_2$CH$_3$), 3.18 (2H, q, 7-CH$_2$CH$_3$), 3.96 (3H, s, 11-OCH$_3$), 5.26 (2H, s, 5-CH$_2$—), 5.43 (2H, s, 17-CH$_2$—), 6.49 (1H, s, 20-OH), 7.30 (1H, s, 14-H), 7.35 (1H, dd, $J_{9,10}$=9.2 Hz, $J_{10,11}$=2.6 Hz, 10-H), 7.55 (1H, d, 12-H), 8.17 (1H, d, 9-H).

REFERENTIAL EXAMPLE 4

7-Methyl-10-hydroxycamptothecin

7-Methyl-10-ethoxycamptothecin (2.0 g, 4.92 mmol) is dissolved, with heating, in 700 ml of 1,1,2,2-tetrachloroethane, and aluminum chloride (1.97 g, 14.8 mmol) is then added to the solution. The mixture is boiled under reflux with stirring for 24 hours. The reaction mixture is concentrated under reduced pressure to dryness, and the residue is subjected to isolation and purification by column chromatography on silica gel (eluent: chloroform-methanol system) and then recrystallized from methanol whereby 0.50 g (26.9%) of the title compound is obtained as yellow prisms.

MP 341°–345.5° C. (d).

IR(KBr): 3395, 1731, 1652, 1591, 1526.

NMR(DMSO-$d_6$) δ ppm: 0.88 (3H, t, J=7.0 Hz, 20-CH$_2$CH$_3$), 1.81–1.92 (2H, m, 20-CH$_2$CH$_3$), 2.75 (3H, s, 7-CH$_3$), 5.24 (2H, s, 5-CH$_2$—), 5.41 (2H, s, 17-CH$_2$—), 6.46 (1H, s, 20-OH), 7.24 (1H, s, 14-H), 7.35 (1H, d, $J_{9,11}$=2.6 Hz, 9-H), 7.41 (1H, dd, 11-H), 8.01 (1H, d, $J_{11,12}$=9.2 Hz, 12-H), 10.29 (1H, br. s, 10-OH).

REFERENTIAL EXAMPLE 5

7-Ethyl-11-hydroxycamptothecin

7-Ethyl-11-methoxycamptothecin (3.0 g, 7.38 mmol) is dissolved in 120 ml of 47% hydrobromic acid and the solution is boiled under reflux for 2.5 hours under a stream of nitrogen. The mixture is concentrated under reduced pressure to dryness, and the residue is isolated and purified by column chromatography on silica gel (eluent: chloroform-methanol system) and recrystallized from ethanol whereby 2.16 g (74.7%) of the title compound is obtained as yellow crystals.

MP >320° C.

IR(KBr): 3500, 3100, 2965, 1741, 1725, 1653, 1590, 1567, 1463, 1256, 1230, 1157, 1143.

NMR(DMSO-$d_6$) δ ppm: 0.89 (3H, t, J=7.3 Hz, 20-CH$_2$CH$_3$), 1.29 (3H, t, J=7.7 Hz, 7-CH$_2$CH$_3$), 1.78–1.95 (2H, m, 20-CH$_2$CH$_3$), 3.14 (2H, q, 7-CH$_2$CH$_3$), 5.23 (2H, s, 5-CH$_2$—), 5.43 (2H, s, 17-CH$_2$—), 6.49 (1H, s, 20-OH), 7.26 (1H, dd, $J_{9,10}$=9.2 Hz, $J_{10,11}$=2.2 Hz, 10-H), 7.27 (1H, s, 14-H), 7.37 (1H, d, 12-H), 8.11 (1H, d, 9-H), 10.35 (1H, s, 11-OH).

REFERENTIAL EXAMPLE 6

7-Isopropyl-9-methoxycamptothecin

Using 2-amino-6-methoxyisobutyrophenone (861 mg, 4.47 mmol), the reaction followed by the after-treatment is carried out in the same manner as in Referential Example 1 whereby 0.80 g (46.9%) of the title compound is obtained.

MP 234°–237° C. (d).

IR(KBr): 3500, 3330, 2950, 1751, 1735, 1665, 1616, 1593, 1568, 1460, 1250, 1232, 1157.

NMR(DMSO-$d_6$) δ ppm: 0.88 (3H, t, J=7.3 Hz, 20-CH$_2$CH$_3$), 1.43 (3H, d, J=7.0 Hz, 7-CH(CH$_3$)CH$_3$), 1.44 (3H, d, J=7.0 Hz, 7-CH(CH$_3$)CH$_3$), 1.78–1.95 (2H, m, 20-CH$_2$CH$_3$), 4.00 (3H, s, 9-OCH$_3$), 4.69–5.15 (1H, m, 7-CH(CH$_3$)$_2$, 5.39 (2H, s, 5-CH$_2$—), 5.43 (2H, s, 17-CH$_2$—), 6.50 (1H, s, 20-OH), 7.18 (1H, dd, J=5.1, 4.0 Hz, 11-H), 7.29 (1H, s, 14-H), 7.70–7.75 (2H, m, 10 and 12-H).

REFERENTIAL EXAMPLE 7

7-Isopropyl-9-hydroxycamptothecin

Using 7-isopropyl-9-methoxycamptothecin (1.3 g, 3.09 mmol), the reaction followed by the after-treatment is carried out in the same manner as in Referential Example 5 whereby 796 mg (63.3%) of the title compound is obtained.

MP 214°–218° C. (d).

IR(KBr): 3265, 2965, 1743, 1653, 1594, 1569, 1286, 1156.

NMR(DMSO-d$_6$) δ ppm: 0.88 (3H, t, J=7.3 Hz, 20-CH$_2$CH$_3$), 1.42 (3H, br. d, 7-CH(CH$_3$)CH$_3$), 1.43 (3H, br. d, 7-CH(CH$_3$)CH$_3$), 1.78–1.95 (2H, m, 20-CH$_2$CH$_3$), 5.10–5.26 (1H, m, 7-CH(CH$_3$)$_2$), 5.40 (2H, s, 5-CH$_2$—), 5.43 (2H, s, 17-CH$_2$—), 6.50 (1H, s, 20-OH), 7.06 (1H, dd, J=6.2, 2.9 Hz, 11-H), 7.29 (1H, s, 14-H), 7.57–7.63 (2H, m, 10 and 12-H), 10.63 (1H, s, 9-OH).

REFERENTIAL EXAMPLE 8

7-Isopropyl-11-methoxycamptothecin

Using 2-amino-4-methoxyisobutyrophenone (861 mg, 4.47 mmol), the reaction followed by the after-treatment is carried out in the same manner as in Referential Example 1 whereby 0.54 g (31.5%) of the title compound is obtained.

MP 195°–196° C. (d).

IR(KBr): 3420, 2965, 1739, 1657, 1622, 1598, 1224, 1154.

NMR(DMSO-d$_6$) δ ppm: 0.88 (3H, t, J=7.3 Hz, 20-CH$_2$CH$_3$), 1.46 (3H, d, J=7.0 Hz, 7-CH(CH$_3$)CH$_3$), 1.47 (3H, d, J=7.0 Hz, 7-CH(CH$_3$)CH$_3$), 1.77–1.95 (2H, m, 20-CH$_2$CH$_3$), 3.90–4.04 (1H, m, 7-CH(CH$_3$)$_2$), 3.96 (3H, s, 11-OCH$_3$), 5.38 (2H, s, 5-CH$_2$—), 5.43 (2H, s, 17-CH$_2$—), 6.50 (1H, s, 20-OH), 7.31 (1H, s, 14-H), 7.35 (1H, dd, J$_{9,10}$=9.5 Hz, J$_{10,12}$=2.9 Hz, 10-H), 7.56 (1H, d, 12-H), 8.30 (1H, d, 9-H).

REFERENTIAL EXAMPLE 9

7-Isopropyl-11-hydroxycamptothecin

Using 7-isopropyl-11-methoxycamptothecin (1.0 g, 2.38 mmol), the reaction followed by the after-treatment is carried out in the same manner as in Referential Example 5 whereby 749 mg (77.5%) of the title compound is obtained.

MP >320° C.

IR(KBr): 3420, 3100, 2970, 1739, 1652, 1618, 1590, 1566, 1245, 1230, 1154.

NMR(DMSO-d$_6$) δ ppm: 0.88 (3H, t, J=7.3 Hz, 20-CH$_2$CH$_3$), 1.45 (3H, d, J=7.0 Hz, 7-CH(CH$_3$)CH$_3$), 1.46 (3H, d, J=7.0 Hz, 7-CH(CH$_3$)CH$_3$), 1.57–1.95 (2H, m, 20-CH$_2$CH$_3$), 3.87–4.02 (1H, m, 7-CH(CH$_3$)$_2$), 5.34 (2H, s, 5-CH$_2$—), 5.42 (2H, s, 17-CH$_2$—), 6.00–6.95 (1H, br, 20-OH), 7.26 (1H, dd, J$_{9,10}$=9.2 Hz, J$_{10,12}$=2.6 Hz, 10-H), 7.28 (1H, s, 14-H), 7.37 (1H, d, 12-H), 8.24 (1H, d, 9-H), 10.38 (1H, br. s, 11-OH).

Preparative Examples where the compounds used in each of the Examples described above are prepared are shown below.

PREPARATIVE EXAMPLE 1

2-Amino-4-fluoropropiophenone 25.0 g (0.21 mol) of boron trichloride is added to 100 ml of dry benzene with ice cooling and stirring, and a solution of 21.3 g (0.19 mol) of 3-fluoroaniline in 200 ml of dry benzene is added to the mixture under a stream of nitrogen. 21.1 g (0.38 mol) of propionitrile and 28.4 g (0.21 mol) of aluminum chloride (ground in a mortar) are added in that order, and the mixture is boiled under reflux for 8 hours. After ice-cooling, 200–220 ml of 2N hydrochloric acid is carefully added, and the mixture is stirred at 80° C. for 1 hour. After cooling, 200 ml of water is added and the mixture is extracted 2–3 times with benzene. The benzene layer is separated, washed with water, dried over anhydrous sodium sulfate and evaporated to dryness under reduced pressure. The residue obtained is isolated and purified by column chromatography on silica gel (eluent: toluene-ethyl acetate system) and recrystallized from ether-n-hexane whereby 19.98 g (62.2%) of the title compound is obtained.

MP 58°–61° C.

IR(KBr): 3420, 3310, 1646, 1620, 1587, 1555, 1435, 1207, 1179, 1128.

NMR(CDCl$_3$) δ ppm: 1.20 (3H, t, J=7.3 Hz, —CH$_2$CH$_3$), 2.93 (2H, q, —CH$_2$CH$_3$), 6.30 (1H, dd, J$_{3,5}$=2.6 Hz, J$_{3,F}$=11.0 Hz, 3-H), 6.34 (1H, ddd, J$_{5,6}$=8.8 Hz, J$_{5,F}$=10.6 Hz, 5-H), 6.45 (2H, br. s, —NH), 7.74 (1H, dd, J$_{6,F}$=6.2 Hz, 6-H).

PREPARATIVE EXAMPLE 2

2-Amino-4-chloropropiophenone

Using 24.5 g (0.19 mol) of 3-chloroaniline, the reaction followed by the after-treatment is carried out in the same manner as in Preparative Example 1 whereby 15.73 g (44.6%) of the title compound is obtained.

MP 73°–75° C.

IR(KBr): 3480, 3445, 3350, 1651, 1638, 1613, 1531, 1200.

NMR(CDCl$_3$) δ ppm: 1.19 (3H, t, J=7.3 Hz, —CH$_2$CH$_3$), 2.93 (2H, q, —CH$_2$CH$_3$), 6.37 (2H, br.s, —NH$_2$), 6.59 (1H, dd, J$_{3,5}$=2.2 Hz, J$_{5,6}$=8.8 Hz, 5-H), 6.46 (1H, d, 3-H), 7.65 (1H, d, 6-H).

PREPARATIVE EXAMPLE 3

2-Amino-4-bromopropiophenone

Using 33.0 g (0.19 mol) of 3-bromoaniline, the reaction followed by the after-treatment is carried out in the same manner as in Preparative Example 1 whereby 20.15 g (46.0%) of the title compound is obtained.

MP 86°–88° C.

IR(KBr): 3490, 3440, 3350, 3320, 1652, 1638, 1609, 1597, 1529, 1209.

NMR(CDCl$_3$) δ ppm: 1.19 (3H, t, J=7.3 Hz, —CH$_2$CH$_3$), 2.93 (2H, q, —CH$_2$CH$_3$), 6.33 (2H, br.s, —NH$_2$), 6.75 (1H, dd, J$_{3,5}$=1.8 Hz, J$_{5,6}$=8.4 Hz, 5-H), 6.83 (1H, d, 3-H), 7.58 (1H, d, 6-H).

PREPARATIVE EXAMPLE 4

2-Amino-4-ethylpropiophenone

Using 23.2 g (0.19 mol) of 3-ethylaniline, the reaction followed by the after-treatment is carried out in the same manner as in Preparative Example 1 whereby 21.10 g (66.7%) of the title compound is obtained.

IR(neat): 3440, 3325, 2960, 2920, 1635, 1615, 1576, 1212.

NMR(CDCl$_3$) δ ppm: 1.20 (3H, t, J=7.3 Hz, 4-CH$_2$CH$_3$), 1.21 (3H, t, J=7.3 Hz, —COCH$_2$CH$_3$), 2.55 (2H, q, 4-CH$_2$CH$_3$), 2.94 (2H, q, —COCH$_2$CH$_3$), 6.1–6.4 (2H, br. s, —NH$_2$), 6.47 (1H, d, J$_{3,5}$=2.2 Hz, 3-H), 6.49 (1H, dd, 5-H), 7.66 (1H, d, J$_{5,6}$=8.1 Hz, 6-H).

PREPARATIVE EXAMPLE 5

2-Amino-4-methoxypropiophenone

Using 23.7 g (0.19 mol) of 3-methoxyaniline, the reaction followed by the after-treatment is carried out in the same manner as in Preparation Example 1 whereby 20.30 g (59.0%) of the title compound is obtained.

MP 54°–56° C.

IR(KBr): 3435, 3320, 1640, 1626, 1602, 1583, 1533, 1456, 1370, 1205, 1142.

NMR(CDCl$_3$) δ ppm: 1.19 (3H, t, J=7.3 Hz, —CH$_2$CH$_3$), 2.90 (2H, q, —CH$_2$CH$_3$), 3.79 (3H, s, —OCH$_3$), 6.07 (1H, d, J$_{3,5}$=2.6 Hz, 3-H), 6.22 (1H, dd, 5-H), 6.41 (2H, br.s, —NH$_2$), 7.67 (1H, d, J$_{5,6}$=8.8 Hz, 6-H).

PREPARATIVE EXAMPLE 6

2-Amino-4-methylthiopropiophenone

Using 26.7 g (0.19 mol) of 3-methylthioaniline, the reaction followed by the after-treatment is carried out in the same manner as in Preparative Example 1 wherein 28.30 g (76.3%) of the title compound is obtained.

MP 75°–76.5° C.

IR(KBr): 3440, 3400, 3300, 2960, 2910, 1642, 1623, 1598, 1573, 1526, 1211.

NMR(CDCl$_3$) δ ppm: 1.20 (3H, t, J=7.3 Hz, —CH$_2$CH$_3$), 2.46 (3H, s, —SCH$_3$), 2.92 (2H, q, —CH$_2$CH$_3$), 6.0–6.8 (2H, br.s, —NH$_2$), 6.42 (1H, d, J$_{3,5}$=1.5 Hz, 3-H), 6.50 (1H, dd, 5-H), 7.63 (1H, d, J$_{5,6}$=8.1 Hz, 6-H).

PREPARATIVE EXAMPLE 7

2-Amino-3-fluoropropiophenone

Using 21.3 g (0.19 mol) of 2-fluoroaniline, the reaction followed by the after-treatment is carried out in the same manner as in Preparative Example 1 wherein 0.82 g (2.8%) of the title compound is obtained.

MP 40°–42° C.

IR(KBr): 3420, 3310, 2970, 2920, 1644, 1625, 1452, 1219.

NMR(CDCl$_3$) δ ppm: 1.21 (3H, t, J=7.3 Hz, —CH$_2$CH$_3$), 2.98 (2H, q, —CH$_2$CH$_3$), 5.6–6.6 (2H, br.s, —NH$_2$), 6.56 (1H, m, 5-H), 7.10 (1H, m, 4-H), 7.54 (1H, m, 6-H).

PREPARATIVE EXAMPLE 8

2-Amino-5-fluoropropiophenone

Using 21.3 g (0.19 mol) of 4-fluoroaniline, the reaction followed by the after-treatment is carried out in the same manner as in Preparative Example 1 wherein 7.00 g (21.8%) of the title compound is obtained.

MP 70°–72° C.

IR(KBr): 3420, 3325, 1636, 1593, 1558, 1483, 1227, 1171.

NMR (CDCl$_3$) δppm: 1.21 (3H, t, J=7.3 Hz, —CH$_2$CH$_3$), 2.93 (2H, q, —CH$_2$CH$_3$), 6.11 (2H, br.s, —NH$_2$), 6.61 (1H, dd, J$_{3,4}$=9.2 Hz, J$_{3,F}$=4.8 Hz, 3-H), 7.03 (1H, ddd, J$_{4,6}$=2.9 Hz, J$_{4,F}$=10.6 Hz, 4-H), 7.41 (1H, dd, J$_{6,F}$=9.9 Hz, 6-H).

PREPARATIVE EXAMPLE 9

2-Amino-5-chloropropiophenone

Using 24.5 g (0.19 mol) of 4-chloroaniline, the reaction followed by the after-treatment is carried out in the same manner as in Preparative Example 1 wherein 3.62 g (10.3%) of the title compound is obtained.

MP 76°–78° C.

IR(KBr): 3430, 3330, 1636, 1618, 1545, 1202.

NMR(CDCl$_3$) δppm: 1.20 (3H, t, J=7.3 Hz, —CH$_2$CH$_3$), 2.94 (2H, q, —CH$_2$CH$_3$), 6.27 (2H, br.s, —NH$_2$), 6.60 (1H, d, J$_{3,4}$=8.8 Hz, 3-H), 7.19 (1H, dd, J$_{4,6}$=2.6 Hz, 4-H), 7.69 (1H, d, 6-H).

PREPARATIVE EXAMPLE 10

2-Amino-5-bromopropiophenone

Using 33.0 g (0.19 mol) of 4-bromoaniline, the reaction followed by the after-treatment is carried out in the same manner as in Preparative Example 1 whereby 3.85 g (8.8%) of the title compound is obtained.

MP 78°–79° C.

IR(KBr): 3430, 3320, 1645, 1621, 1208.

NMR(CDCl$_3$) δppm: 1.20 (3H, t, J=7.3 Hz, —CH$_2$CH$_3$), 2.94 (2H, q, —CH$_2$CH$_3$), 6.28 (2H, br.s, —NH$_2$), 6.56 (1H, d, J$_{3,4}$=8.8 Hz, 3-H), 7.31 (1H, dd, J$_{4,6}$=2.2 Hz, 4-H), 7.84 (1H, d, 6-H).

PREPARATIVE EXAMPLE 11

2-Amino-5-methylpropiophenone

Using 20.6 g (0.19 mol) of 4-methylaniline, the reaction followed by the after-treatment is carried out in the same manner as in Preparative Example 1 wherein 12.44 g (40.2%) of the title compound is obtained.

MP 75.5°–76.5° C.

IR(KBr): 3430, 3315, 2965, 2900, 1635, 1587, 1553, 1226, 1193.

NMR (CDCl$_3$) δppm: 1.20 (3H, t, J=7.3 Hz, —CH$_2$CH$_3$), 2.26 (3H, s, —CH$_3$), 2.97 (2H, q, —CH$_2$CH$_3$), 5.9–6.4 (2H, br. s, —NH$_2$), 6.59 (1H, d, J$_{3,4}$=8.1 Hz, 3-H), 7.09 (1H, dd, 4-H), 7.53 (1H, d, J$_{4,6}$=1.5 Hz, 6-H).

PREPARATIVE EXAMPLE 12

2-Amino-5-methylthiopropiophenone

Using 26.7 (0.19 mol) of 4-methylthioaniline, the reaction followed by the after-treatment is carried out in the same manner as in Preparative Example 1 whereby 20.60 g (55.6%) of the title compound is obtained.

MP 64.5°–65.5° C.

IR(KBr): 3430, 3315, 2965, 2900, 1635, 1618, 1578, 1540, 1205, 1158.

NMR(CDCl$_3$) δppm: 1.21 (3H, t, J=7.3 Hz, —CH$_2$CH$_3$), 2.42 (3H, s, —SCH$_3$), 2.98 (2H, q, —CH$_2$CH$_3$), 6.1–6.6 (2H, br.s, —NH$_2$), 6.63 (1H, d, J$_{3,4}$=8.1 Hz, 3-H), 7.32 (1H, dd, 4-H), 7.82 (1H, d, J$_{4,6}$=2.2 Hz, 6-H),

PREPARATIVE EXAMPLE 13

2-l-Amino-4,5-dichloropropiophenone

Using 31.1 g (0.19 mol) of 3,4-dichloroaniline, the reaction followed by the after-treatment is carried out in the same manner as in Preparative Example 1 whereby 1.63 g (3.9%) of the title compound is obtained.

MP 88°–89° C.

IR(KBr): 3420, 3325, 1648, 1609, 1577, 1521, 1457, 1204.

NMR(CDCl$_3$): δppm: 1.20 (3H, t, J=7.3 Hz, —CH$_2$CH$_3$), 2.93 (2H, q, —CH$_2$CH$_3$), 6.30 (2H, br.s, —NH$_2$), 6.78 (1H, s, 3-H), 7.79 (1H, s, 6-H).

PREPARATIVE EXAMPLE 14

2-Amino-4,6-dimethoxypropiophenone

Using 29.4 g (0.19 mol) of 3,5-dimethoxyaniline, the reaction followed by the after-treatment is carried out in the same manner as in Preparative Example 1 whereby 36.76 g (91.5%) of the title compound is obtained.

MP 63°–66° C.

IR(KBr): 3420, 3300, 2970, 2915, 1608, 1570, 1205, 1161, 1140.

NMR(CDCl$_3$) δppm: 1.12 (3H, t, J=7.3 Hz, —CH$_2$CH$_3$), 2.91 (2H, q, —CH$_2$CH$_3$), 3.77 (b 3H, s, 4 or 6-OCH$_3$), 3.81 (3H, s, 4 or 6-OCH$_3$), 5.72 (1H, d, J$_{3,4}$=2.2 Hz, 3-H), 5.77 (1H, d, 5-H), 6.24 (2H, br. s, —NH$_2$).

PREPARATIVE EXAMPLE 15

2-Amino-3,6-dimethoxypropiophenone

Using 29.4 g (0.19 mol) of 2,5-dimethoxyaniline, the reaction followed by the after-treatment is carried out in the same manner as in Preparative Example 1 whereby 2.46 g (6.1%) of the title compound is obtained as an oil.

IR(neat): 3470, 3345, 2930, 2818, 1628, 1608, 1538, 1471, 1353, 1259, 1224, 1108.

NMR(CDCl$_3$) δppm: 1.14 (3H, t, J=7.3 Hz, —CH$_2$CH$_3$), 2.95 (2H, q, —CH$_2$CH$_3$), 3.77 (3H, s, 3 or 6-OCH$_3$), 3.78 (3H, s, 3 or 6-OCH$_3$), 6.05 (1H, d, J$_{4,5}$=8.8 Hz, 5-H), 6.07 (2H, br.s, —NH$_2$) 6.70 (1H, d, 4-H).

PREPARATIVE EXAMPLE 16

2-Amino-4,5-dimethoxypropiophenone

Using 29.4 g (0.19 mol) of 3,4-dimethoxyaniline, the reaction followed by the after-treatment is carried out in the same manner as in Preparative Example 1 whereby 24.27 g (60.4%) of the title compound is obtained.

MP 128°–129° C.

IR(KBr): 3420, 3320, 1627, 1589, 1539, 1506, 1449, 1394, 1231, 1198, 1152.

NMR(CDCl$_3$) δppm: 1.21 (3H, t, J=7.3 Hz, —CH$_2$CH$_3$), 2.90 (2H, q, —CH$_2$CH$_3$), 3.83 (3H, s, 4 or 5-OCH$_3$), 3.87 (3H, s, 4 or 5-OCH$_3$), 5.6–6.9 (2H,br, —NH$_2$), 6.11 (1H, s, 3-H), 7.16 (1H, s, 6-H).

PREPARATIVE EXAMPLE 17

2-Amino-4,5,6-trimethoxypropiophenone

Using 35.2 g (0.19 mole) of 3,4,5-trimethoxyaniline, the reaction followed by the after-treatment is carried out in the same manner as in Preparative Example 1 wherein 6.52 g (14.2%) of the title compound is obtained.

MP 75°–77° C.

IR(KBr): 3460, 3310, 2970, 2910, 1635, 1610, 1571, 1543, 1449, 1242, 1199, 1121.

NMR(CDCl$_3$) δppm: 1.15 (3H, t, J=7.3 Hz, —CH$_2$CH$_3$), 2.94 (2H, q, —CH$_2$CH$_3$), 3.76 (3H, s, 4, 5 or 6-OCH$_3$), 3.83 (3H, s, 4, 5 or 6-OCH$_3$), 3.93 (3H, s, 4, 5 or 6-OCH$_3$), 5.84 (2H, br.s, —NH$_2$), 5.89 (1H, s, 3-H).

PREPARATIVE EXAMPLE 18

2-Amino-4-dimethylaminopropiophenone

Using 35.0 g (0.19 mol) of 3-dimethylaminoaniline hydrochloride, the reaction is carried out in the same manner as in Preparative Example 1. After completion of the reaction, the aqueous layer is made alkaline with an aqueous sodium hydroxide solution and extracted with benzene or ethyl acetate. The after-treatment is carried out in the same manner whereby 5.45 g (11.9%) of the title compound is obtained.

MP 106°–107.5° C.

IR (KBr): 3400, 3300, 2955, 2910, 1605, 1512, 1382, 1242, 1156.

NMR(CDCl$_3$) δppm: 1.19 (3H, t, J=7.3 Hz, —CH$_2$CH$_3$), 2.86 (2H, q, —CH$_2$CH$_3$), 3.00 (6H, s, —N(CH$_3$)$_2$), 5.76 (1H, d, J$_{3,5}$=2.2 Hz, 3-H), 6.07 (1H, dd, 5-H), 6.2–6.5 (2H, br.s, —NH$_2$), 7.61 (1H, d, J$_{5,6}$=9.5 Hz, 6-H).

PREPARATIVE EXAMPLE 19

2-Amino-5-dimethylaminopropiophenone

Using 26.1 g (0.19 mol) of 4-dimethylaminoaniline, the reaction followed by the after-treatment is carried out in the same manner as in Preparative Example 18 whereby 4.86 g (13.2%) of the title compound is obtained.

MP 98.5°–99.5° C.

IR(KBR): 3450, 3330, 2965, 2920, 2895, 2790, 1639, 1571, 1555, 1499, 1205.

NMR(CDCl$_3$) δppm: 1.21 (3H, t, J=7.3 Hz, —CH$_2$CH$_3$), 2.83 (6H, s, —N(CH$_3$)$_2$), 2.98 (2H, q, —CH$_2$CH$_3$), 5.7–6.0 (2H, br.s, -NH$_2$), 6.64 (1H, d, J$_{3,4}$=8.8 Hz, 3-H), 6.98 (1H, dd, 4-H), 7.14 (1H, d, J$_{4,6}$=2.2 Hz, 6-H).

PREPARATIVE EXAMPLE 20

2,4-Diaminopropiophenone and 2,6-diaminopropiophenone

Using 19.9 g (0.19 mol) of 1,3-phenylenediamine, the reaction followed by the after-treatment is carried out in the same manner as in Preparative Example 18 whereby the title compounds, i.e. 5.20 g (17.0%) of 2,4-diaminopropiophenone and 1.35 g (4.4%) of 2,6-diaminopropiophenone, are obtained.

2,4-Diaminopropiophenone

MP 155°–157° C.

IR(KBr): 3410, 3330, 3210, 2970, 2920, 2900, 1615, 1566, 1527, 1439, 1374, 1236, 1155.

NMR(CDCl$_3$) δppm: 1.18 (3H, t, J=7.3 Hz, —CH$_2$CH$_3$), 2.86 (2H, q, —CH$_2$CH$_3$), 5.81 (1H, d, J$_{3,5}$=2.2 Hz, 3-H), 5.96 (1H, dd, 5-H), 7.56 (1H, d, J$_{5,6}$=8.1 Hz, 6-H).

2,6-Diaminopropiophenone

MP 65°–66.5° C.

IR(KBr): 3440, 3350, 1589, 1456, 1212.

NMR(CDCl$_3$) δppm: 1.21 (3H, t, J=7.3 Hz, —CH$_2$CH$_3$), 2.93 (2H, q, —CH$_2$CH$_3$), 4.2–4.8 (4H, br. s, —NH$_2$x2), 6.06 (2H, d, J=7.3 Hz, 3 and 5-H), 6.95 (1H, t, 4-H).

PREPARATIVE EXAMPLE 21

2-Amino-3-fluoroacetophenone

Using 21.3 g (0.19 mol) of 2-fluoroaniline and 15.7 g (0.38 mol) of acetonitrile, the reaction followed by the after-treatment is carried out in the same manner as in Preparative Example 1 whereby 0.99 g (3.4%) of the title compound is obtained.

MP 60°–61.5° C.

IR(KBr): 3440, 3350, 1629, 1551, 1452, 1262.

NMR(CDCl$_3$) δppm: 2.58 (3H, s, —CH$_3$), 6.0–6.6 (2H, br.s, -NH$_2$), 6.57 (1H, m, 5-H), 7.11 (1H, m, 4-H), 7.51 (1H, dd, J$_{4,6}$=1.5 Hz, J$_{5,6}$=8.1 Hz, 6-H).

PREPARATIVE EXAMPLE 22

2-Amino-4-bromoacetophenone

Using 33.0 g (0.19 mol) of 3-bromoaniline, the reaction followed by the after-treatment is carried out in the same manner as in Preparative Example 21 whereby 14.39 g (34.9%) of the title compound is obtained.

MP 81.5°–84.5° C.

IR(KBr): 3410, 3300, 1633, 1608, 1532, 1234.

NMR(CDCl$_3$) δppm: 2.54 (3H, s, —CH$_3$), 6.1–6.5 (2H, br. s, —NH$_2$), 6.75 (1H, dd, J$_{3,5}$=1.5 Hz, J$_{5,6}$=8.1 Hz, 5-H), 6.83 (1H, d, 3-H), 7.54 (1H, d, 6-H).

PREPARATIVE EXAMPLE 23

2-Amino-5-ethoxyacetophenone

Using 26.3 g (0.19 mol) of 4-ethoxyaniline, the reaction followed by the after-treatment is carried out in the same manner as in Preparative Example 21 whereby 2.17 g (6.3%) of the title compound is obtained.

MP 94°–95° C.

IR(KRr): 3450, 3330, 2965, 1634, 1561, 1551, 1200.

NMR(CDCl$_3$) δppm: 1.40 (3H, t, J=7.3 Hz, —CH$_2$CH$_3$), 2.56 (3H, s, —CH$_3$), 3.99 (2H, q, —CH$_2$CH$_3$), 5.7–6.2 (2H, br.s, —NH$_2$), 6.62 (1H, d, J$_{3,4}$=8.8 Hz, 3-H), 6.97 (1H, dd, 4-H), 7.20 (1H, d, J$_{4,6}$=2.9 Hz, 6-H).

PREPARATIVE EXAMPLE 24

2-Amino-4-chlorobutyrophenone

Using 24.5 g (0.19 mol) of 3-chloroaniline and 26.5 g (0.38 mol) of butyronitrile, the reaction followed by the after-treatment is carried out in the same manner as in Preparative Example 1 whereby 16.53 g (43.5%) of the title compound is obtained.

MP 44°–46° C.

IR(KBr): 3450, 3340, 2960, 1639, 1609, 1577, 1537, 1423, 1203.

NMR(CDCl$_3$) δppm: 1.00 (3H, t, J=7.3 Hz, —CH$_2$CH$_2$CH$_3$), 1.74 (2H, tq, J=7.3 Hz, —CH$_2$CH$_2$CH$_3$), 2.87 (2H, t, J=7.3 Hz, —CH$_2$CH$_2$CH$_3$), 6.36 (2H, br.s, —NH$_2$), 6.60 (1H, dd, J$_{3,5}$=2.2 Hz, J$_{5,6}$=8.8 Hz, 5-H), 6.64 (1H, d, 3-H), 7.66 (1H, d, 6H).

PREPARATIVE EXAMPLE 25

2-Amino-5-methylbutyrophenone

Using 20.6 g (0.19 mol) of 4-methylaniline, the reaction followed by the after-treatment is carried out in the same manner as in Preparative Example 24 whereby 20.79 g (61.0%) of the title compound is obtained.

MP 65°–67° C.

IR(KBr): 3440, 3330, 1632, 1575, 1557, 1547, 1222, 1186, 1160.

NMR(CDCl$_3$) δppm: 1.01 (3H, t, J=7.3 Hz, —CH$_2$CH$_2$CH$_3$), 1.75 (2H, tq, J=7.3 Hz, —CH$_2$CH$_2$CH$_3$) 2.26 (3H, s, —CH$_3$), 2.90 (2H, t, J=7.3 Hz, —CH$_2$CH$_2$CH$_2$), 6.10 (2H, br.s, —NH$_2$), 6.58 (1H, d, J$_{3,4}$=8.1 Hz, 3-H), 7.08 (1H, dd, 4-H), 7.52 (1H, d, J$_{4,6}$=1.5 Hz, 6-H).

PREPARATIVE EXAMPLE 26

2-Amino-3-bromoisobutyrophenone

Using 33.0 g (0.19 mol) of 2-bromoaniline and 26.5 g (0.38 mol) of isobutyronitrile, the reaction followed by the after-treatment is carried out in the same manner as in Preparative Example 1 whereby 4.38 g (9.4%) of the title compound is obtained as an oil.

IR(neat): 3450, 3320, 2960, 1646, 1602, 1561, 1531, 1217.

NMR(CDCl$_3$) δppm: 1.20 (6H, d, J=7.0 Hz, —CH(CH$_3$)$_2$), 3.51–3.63 (1H, m, —CH(CH$_3$)$_2$), 6.53 (1H, dd, J$_{4,5}$=7.7 Hz, J$_{5,6}$=8.1 Hz, 5-H) 6.93 (2H, br.s, —NH$_2$), 7.56 (1H, dd, J$_{4,6}$=1.5 Hz, 4-H), 7.75 (1H, dd, 6-H).

PREPARATIVE EXAMPLE 27

2-Amino-4-methoxyisobutyrophenone and 2-amino-6-methoxyisobutyrophenone

Using 23.7 g (0.19 mol) 3-methoxyaniline, the reaction followed by the after-treatment is carried out in the same manner as in Preparative Example 26 whereby the title compounds, i.e. 24.75 g (66.8%) of 2-amino-4-methoxyisobutyrophenone and 2.40 g (6.5%) of 2-amino-6-methoxyisobutyrophenone as an oil, are obtained.

2-Amino-4-methoxyisobutyrophenone

MP 69°–70° C.

IR(KBr): 3400, 3300, 2960, 1607, 1532, 1457, 1384, 1212, 1134.

NMR(CDCl$_3$) δppm: 1.19 (6H, d, J=7.0 Hz, —CH(CH$_3$)$_2$), 3.51 (1H, qq, —CH(CH$_3$)$_2$), 3.80 (3H, s, —OCH$_3$), 6.08 (1H, d, J$_{3,5}$=2.6 Hz, 3-H), 6.23 (1H, dd, 5-H), 6.45 (2H, br.s, —NH$_2$), 7.70 (1H, d, J$_{5,6}$=9.2 Hz, 6-H).

2-Amino-6-methoxyisobutyrophenone

IR(neat): 3460, 3360, 2960, 1609, 1576, 1465, 1268, 1133.

NMR(CDCl$_3$) δppm: 1.12 (6H, d, J=7.0 Hz, —CH(CH$_3$)$_2$), 3.49 (1H, qq, —CH(CH$_3$)$_2$), 3.81 (3H, s, —OCH$_3$), 5.12 (2H, br.s, —NH$_2$), 6.22 (1H, dd, J$_{3,4}$=8.1 Hz, J$_{3,5}$=1.1 Hz, 3-H), 6.26 (1H, dd, J$_{4,5}$=8.1 Hz, 5-H), 7.08 (1H, dd, 4-H).

PREPARATIVE EXAMPLE 28

2-Amino-5-bromovalerophenone

Using 33.0 g (0.19 mol) of 4-bromoaniline and 31.8 g (0.38 mol) of valeronitrile, the reaction followed by the after-treatment is carried out in the same manner as in Preparative Example 1 whereby 10.70 g (21.8%) of the title compound is obtained.

MP 74°–76° C.

IR(KBr): 3440, 3330, 2950, 1640, 1609, 1581, 1530, 1194.

NMR(CDCl$_3$) δppm: 0.96 (3H, t, J=7.3 Hz, —CH$_2$CH$_2$CH$_2$CH$_3$), 1.34–1.46 (2H, m, —CH$_2$CH$_2$CH$_2$CH$_3$), 1.63–1.74 (2H, m, —CH$_2$CH$_2$CH$_2$CH$_3$), 2.89 (2H, t, J=7.3 Hz, —CH$_2$CH$_2$CH$_2$CH$_3$), 6.29 (2H, br.s, —NH$_2$), 6.55 (1H, d, J$_{3,4}$=8.8 Hz, 3-H), 7.31 (1H, dd, 4-H), 7.82 (1H, d, J$_{4,6}$=2.6 Hz, 6-H).

PREPARATIVE EXAMPLE 29

2-Amino-5-nitropropiophenone 1.0 g (6.7 mmol) of 2-aminopropiophenone is dissolved in 15 ml of concentrated sulfuric acid, and 1 ml of a solution of 746 mg (7.4 mmol) potassium nitrate in concentrated sulfuric acid is added dropwise at −10° C. over 30 minutes and the mixture is stirred at −10° C. for 30 minutes. After the reaction, the reaction solution is poured into ice-water and the mixture is extracted three times each with 200 ml of chloroform, and the extracts are combined and dried over anhydrous magnesium sulfate. The solvent is distilled off under reduced pressure, and the residue is subjected to column chromatography on silica gel (eluant: ether—n-hexane 1:1) and then recrystallized from ether whereby 30 (2.3%) of the title compound is obtained.

MP 74.5°–76° C.

IR(KBr): 3410, 3050, 2970, 2920, 1634, 1527, 1502, 1337.

NMR(CDCl$_3$) δppm: 1.55 (3H, t, J=7.3 Hz, —CH$_2$CH$_3$), 3.31 (2H, q, —CH$_2$CH$_3$), 7.64 (1H, d, J$_{3,4}$=9.5 Hz, 3-H), 8.06 (1H, dd, 4-H), 8.63 (1H, d, J$_{4,6}$=2.2 Hz, 6-H).

PREPARATIVE EXAMPLE 30

2-Amino-4-cyanopropiophenone 10.0 g (43.8 mmol) of 2-amino-4-bromopropiophenone obtained in Preparative Example 3 is dissolved in 10 ml of dimethylformamide, and 4.3 g (48.2 mmol) of cuprous cyanide is added. The mixture is stirred at 170° C. for 2 hours in nitrogen atmosphere. After cooling, chloroform is added to the reaction mixture and insoluble matters are filtered off. The filtrate is extracted several times with chloroform. The chloroform extracts are combined, washed with water, dried over anhydrous are combined, washed with water, dried over anhydrous sodium sulfate and evaporated to dryness under reduced pressure. The residue obtained is isolated and purified by column chromatography on silica gel (eluent: chloroform—n-hexane 1:1) and then recrystallized from ether-n-hexane whereby 4.4 g (58.0% of the title compound is obtained.

MP 118°–120° C.

IR(KBr): 3420, 3320, 2225, 1651, 1610, 1581, 1204.

NMR(CDCl$_3$) δppm: 1.21 (3H, t, J=7.3 Hz, —CH$_2$CH$_3$), 2.98 (2H, q, —CH$_2$CH$_3$), 6.43 (2H, br.s, —NH$_2$), 6.87 (1H, dd, J$_{3,5}$=1.5 Hz, J$_{5,6}$=8.8 Hz, 5-H), 6.94 (1H, d, 3-H), 7.82 (1H, d, 6-H).

PREPARATIVE EXAMPLE 31

2-Amino-5-cyanopropiophenone

Using 2.3 g (10.0 mmol) 2-amino-5-bromopropiophenone, 1.0 g (11.0 mmol) of cuprous cyanide and 2.3 ml of dimethylformamide, the reaction followed by the after-treatment is carried out in the same manner as in Preparative Example 30 whereby 0.78 g (44.8%) of the title compound is obtained.

MP 130.5°–131.5° C.

IR(KBr): 3420, 3310, 2215, 1625.

NMR(CDCl$_3$) δppm: 1.22 (3H, t, J=7.3 Hz, —CH$_2$CH$_3$), 2.97 (2H, q, —CH$_2$CH$_3$), 6.45-7.20 (2H, br, —NH$_2$), 6.67 (1H, d, J$_{3,4}$=8.4 Hz, 3-H), 7.44 (1H, dd, 4-H), 8.08 (1H, d, J$_{4,6}$=1.8 Hz, 6-H).

PREPARATIVE EXAMPLE 32

2,5-Diaminopropiophenone

Using 19.9 g (0.19 mol) of 1,4-phenylenediamine, the reaction followed by the after-treatment is carried out in the same manner as in Preparative Example 18 whereby 7.30 g (23.8%) of the title compound is obtained.

MP 132°–135° C.

IR(KBr): 3380, 3378, 3220, 2960, 2915, 2900, 1644, 1562, 1491, 1263, 1199.

NMR(CDCl$_3$) δppm: 1.20 (3H, t, J=7.3 Hz, —CH$_2$CH$_3$), 2.93 (2H, q, —CH$_2$CH$_3$), 6.57 (1H, d, J$_{3,4}$=8.8 Hz, 3-H), 6.78 (1H, dd, 4-H), 7.11 (1H, d, J$_{4,6}$=2.2 Hz, 6-H).

PREPARATIVE EXAMPLE 33

2-Amino-4-fluoro-5-methoxypropiophenone

Using 3-fluoro-4-methoxyaniline (27.1 g, 0.19 mol), the reaction followed by the after-treatment is carried out in the same manner as Preparative Example 1 whereby 26.4 g (69.7%) of the title compound is obtained.

MP 96.5°–97.5° C.

IR(KBr)cm: 3420, 3325, 1644, 1590, 1555, 1507, 1241, 1197, 1150.

NMR(CDCl$_3$) δppm: 1.21 (3H, t, J=7.3 Hz, —COCH$_2$CH$_3$), 2.92 (2H, q, —COCH$_2$CH$_3$), 3.85 (3H, s, —OCH$_3$), 6.07-6.28 (2H, br, —NH$_2$), 6.39 (1H, d, J$_{3,F}$=12.8 Hz, 3-H), 7.31 (1H, d, J$_{6,F}$=9.5 Hz, 6-H).

It is understood that the preceeding representative examples may be varied within the scope of the present specification, both as to the reactants and conditions, by one skilled in the art to achieve essentially the same results.

As many apparently widely different embodiments of the present invention may be made without departing from the spirit and scope thereof, it is to be construed that the present invention is not limited to the specific embodiments thereof as defined in the appended claims.

What is claimed is:

1. Camptothecin derivatives represented by the formula:

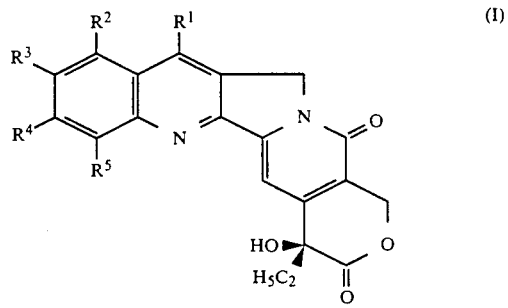

wherein $R^1$ represents a lower alkyl group, $R^2$ represents a hydrogen atom or an amino, hydroxyl, lower acylamino or lower alkoxy group, $R^3$ represents a hydrogen or halogen atom or a lower alkyl, hydroxyl, lower alkoxy, nitro, amino, cyano or di(lower alkyl)amino group, $R^4$ represents a hydrogen or halogen atom or a lower alkyl, hydroxyl, lower alkoxy, lower alkylthio, amino, cyano or di(lower alkyl)amino group, and $R^5$ represents a hydrogen or halogen atom or a hydroxyl or lower alkoxy group, with the proviso that all of the $R^2$, $R^3$, $R^4$ and $R^5$ substituents should not simultaneously be a hydrogen atom and also that if any of the $R^2$, $R^3$, $R^4$ and $R^5$ is a hydroxyl or lower alkoxy group, all of the other three substituents should not simultaneously be a hydrogen atom and also that if $R^3$ is a halogen atom, a nitro group or an amino group, all of the $R^2$, $R^4$ and $R^5$ substituents should not simultaneously be a hydrogen atom.

2. Camptothecin derivatives according to claim 1, wherein any two of the $R^2$, $R^3$, $R^4$ and $R^5$ substituents are hydroxyl and/or lower alkoxy group and the other substituents are hydrogen atoms.

3. Camptothecin derivatives according to claim 1, wherein any one of the $R^2$, $R^3$, $R^4$ and $R^5$ substituents is a lower alkyl group which may be the same as or different from $R^1$.

* * * * *